US011517657B2

(12) United States Patent
Monty et al.

(10) Patent No.: US 11,517,657 B2
(45) Date of Patent: *Dec. 6, 2022

(54) COMBINATION SUCTION AND IRRIGATION HAND TOOL

(71) Applicant: Camodo, LLC, West Bend, WI (US)

(72) Inventors: Charles J. Monty, Milwaukee, WI (US); Philippe A. Capraro, Denver, CO (US); Thomas S. Doig, West Bend, WI (US); Robert Guba, Bridgeport, CT (US)

(73) Assignee: Camodo, LLC, West Bend, WI (US)

( * ) Notice: Subject to any disclaimer, the term of this patent is extended or adjusted under 35 U.S.C. 154(b) by 148 days.

This patent is subject to a terminal disclaimer.

(21) Appl. No.: 16/411,954

(22) Filed: May 14, 2019

(65) Prior Publication Data

US 2019/0269845 A1 Sep. 5, 2019

Related U.S. Application Data

(63) Continuation of application No. 14/612,279, filed on Feb. 2, 2015, now Pat. No. 10,286,141.

(Continued)

(51) Int. Cl.
*A61M 3/02* (2006.01)
*A61M 1/00* (2006.01)

(52) U.S. Cl.
CPC ........ *A61M 3/0262* (2013.01); *A61M 1/7411* (2021.05); *A61M 1/774* (2021.05);
(Continued)

(58) Field of Classification Search
CPC ............. A61M 1/0064; A61M 1/0045; A61M 1/0047; A61M 3/0262; A61M 2205/3334;
(Continued)

(56) References Cited

U.S. PATENT DOCUMENTS 3,105,619 A * 10/1963 Rohrmuller ........... B05B 9/0822
222/209
4,519,385 A * 5/1985 Atkinson ............ A61M 1/0064
601/161

(Continued)

*Primary Examiner* — William R Carpenter
*Assistant Examiner* — Justin L Zamory
(74) *Attorney, Agent, or Firm* — Boyle Fredrickson S.C.

(57) ABSTRACT

An irrigation fluid dispensing tool well suited for use in a combination suction and irrigation tool has a frame carrying a surge flow pump formed of a flow controller of a manipulable handgrip of the tool handle, compressible irrigation fluid reservoir, and frame where the flow controller preferably is formed of a handle lever of the handgrip that is displaceable, preferably pivotable, between one or more of a surge flow actuation position, flow obstructing actuation position, and flow initiating position. The lever actuates a valve, preferably a pinch valve, when displaced toward the flow obstructing actuation position. The lever actuates the surge pump by compressing the reservoir, preferably squeeze bulb, against the frame when the handgrip is squeezed. The lever can be assembled to the frame in a protective shipping and storage position and is movable to a tool operating position providing irrigation fluid flow control during tool operation.

40 Claims, 12 Drawing Sheets

Related U.S. Application Data

(60) Provisional application No. 61/946,855, filed on Mar. 2, 2014, provisional application No. 61/934,099, filed on Jan. 31, 2014.

(52) U.S. Cl.
CPC .......... *A61M 3/022* (2014.02); *A61M 3/0208* (2014.02); *A61M 3/0216* (2014.02); *A61M 3/0279* (2013.01); *A61M 2205/3334* (2013.01)

(58) Field of Classification Search
CPC . A61C 17/02; A61C 17/0202; B05B 11/0048; B67D 7/0216
See application file for complete search history.

(56) References Cited

U.S. PATENT DOCUMENTS

| | | | |
|---|---|---|---|
| 2005/0025646 A1* | 2/2005 | Miller | F04B 43/02 417/472 |
| 2013/0165849 A1* | 6/2013 | Monty | A61M 1/0064 604/30 |

* cited by examiner

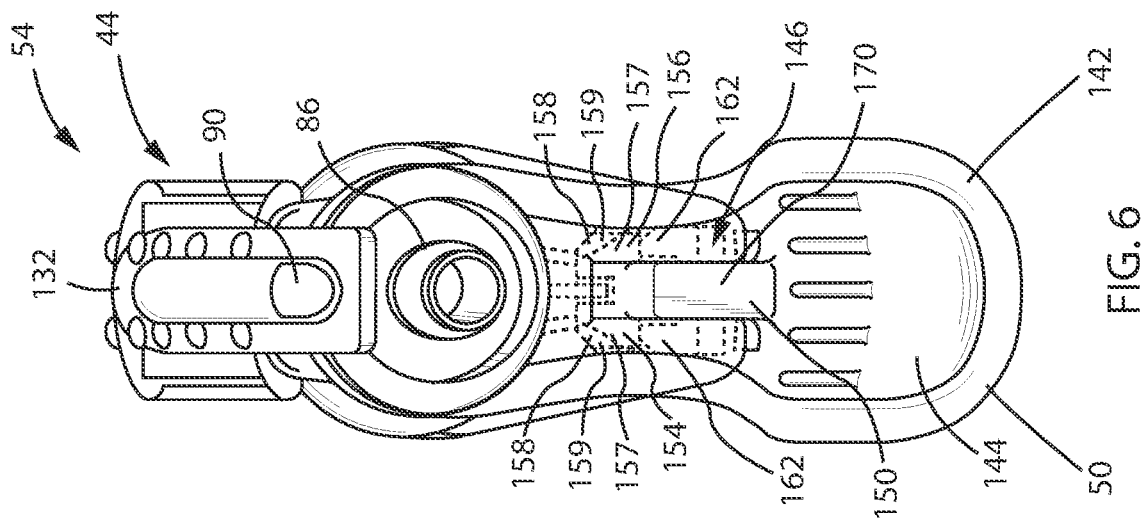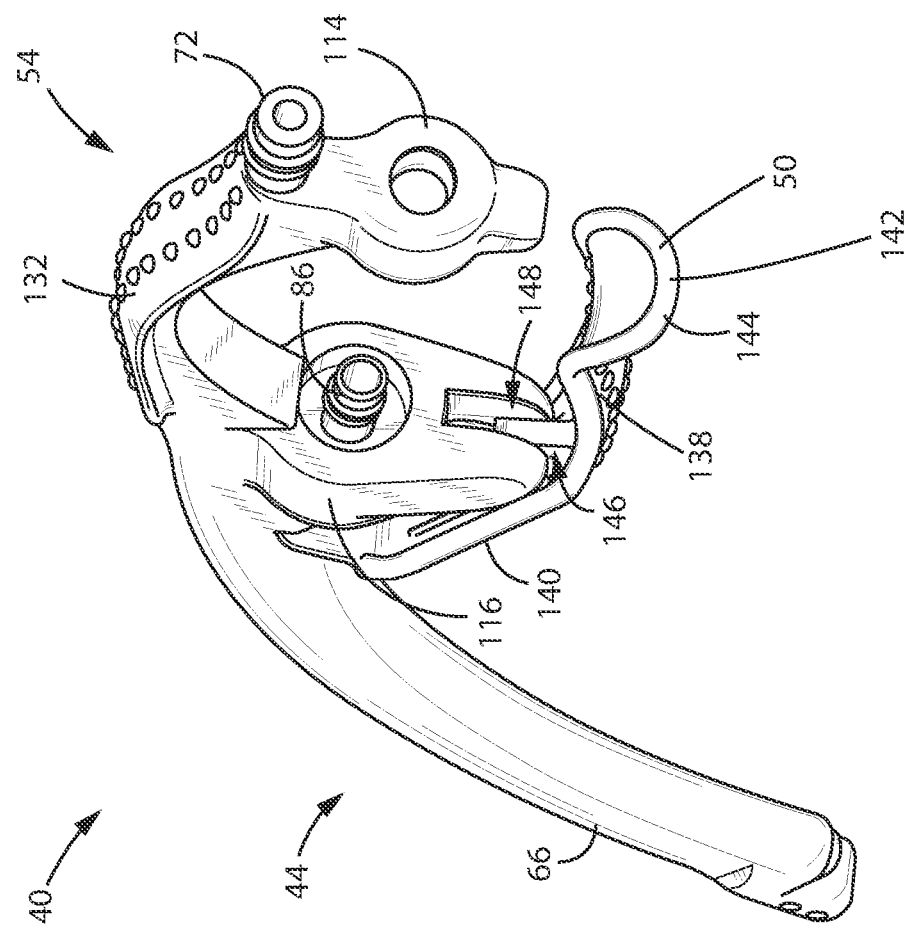

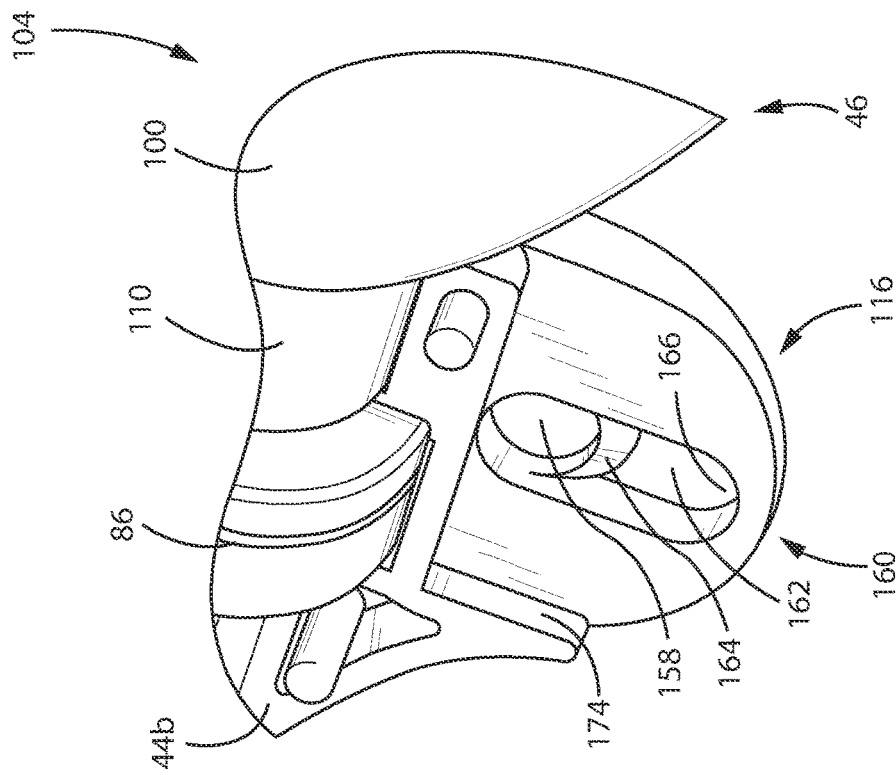
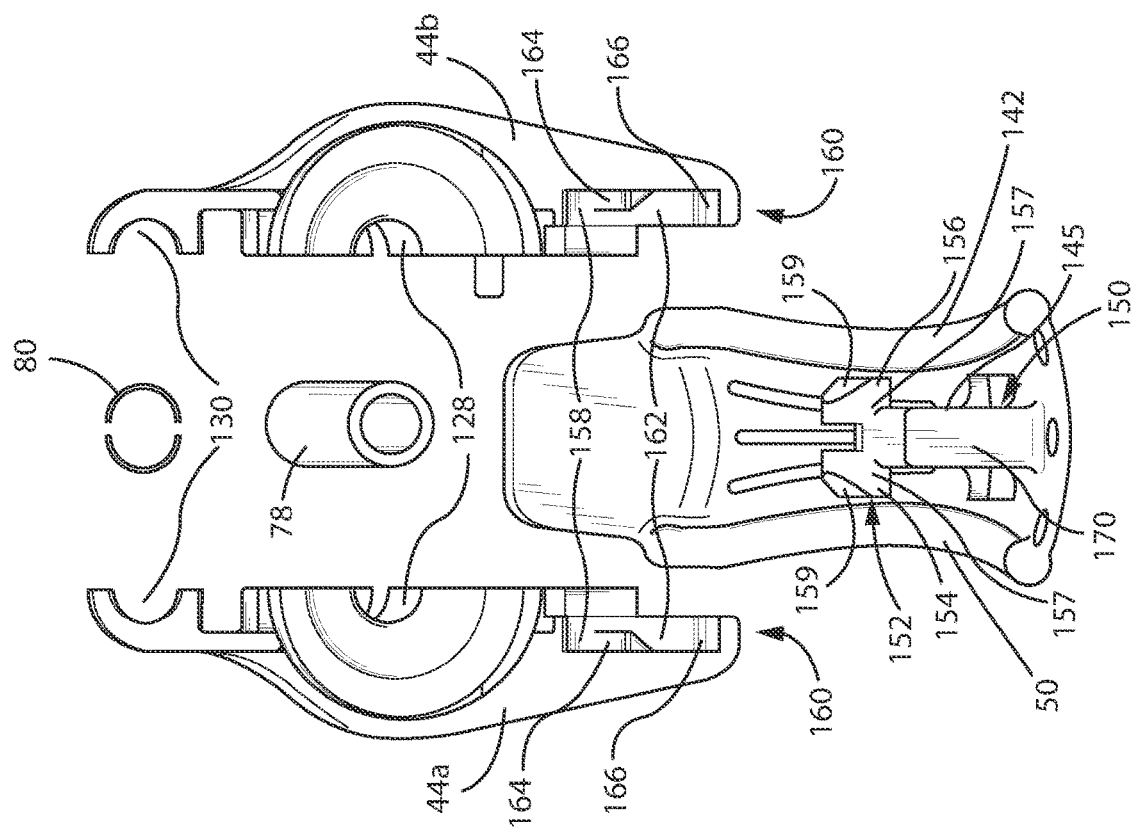

COMBINATION SUCTION AND IRRIGATION HAND TOOL

CROSS REFERENCE

This application is a continuation of U.S. Non-Provisional patent application Ser. No. 14/612,279, filed on Feb. 2, 2015, which issued as U.S. Pat. No. 10,286,141 on May 14, 2019, and which claims priority in U.S. Provisional Patent Application No. 61/934,099 filed Jan. 31, 2014, and U.S Provisional Patent Application No. 61/946,855 filed Mar. 2, 2014, under 35 U.S.C. § 119(e), the entire disclosure of each of which is hereby expressly incorporated herein by reference.

FIELD

The present invention is directed to an irrigation tool usable for medical and dental applications and more particularly to an irrigation tool that provides greater irrigation fluid flow control and which can include suctioning capabilities.

BACKGROUND

Yankauer suckers used for suctioning fluids such as blood or saline solution, during surgical, dental, and other medical applications have enjoyed widespread commercial success. Likewise, syringe and bulb type irrigators used for dispensing saline solution or other irrigation or antiseptic fluids during surgery, dental procedures, and other medical applications have enjoyed widespread commercial success.

In the past, many companies and individuals have attempted to develop a single tool or device that is not only capable of providing suction but which also is capable of providing irrigation. Very few, if any, have enjoyed any kind of commercial success because their designs are complicated, unduly expensive, or are ergonomically unwieldy. Additionally, these attempts yielded devices that are aesthetically, ergonomically and/or functionally quite undesirably different than Yankauer suckers and syringe/bulb irrigators used for suction and/or irrigation in a typical surgical and/or dental suite. This is highly relevant as many doctors, surgeons and other medical professionals have a tendency to be change adverse, therefore, a radical change in a tool that performs a given procedure or function may not be accepted as readily as would a tool that more closely emulates the current look, feel and procedure or function of the tool(s) currently in use.

One such attempt that improves over prior attempts to produce a combination hand held irrigation and suction tool is disclosed in commonly owned U.S. application Ser. No. 13/817,958, entitled "Hand Held Suction and Irrigation Tool" published as U.S. Patent Application Publication No. US 2013/0165849, the entirety of which is expressly incorporated by reference herein. The combination tool disclosed in the '958 application dramatically improves upon prior attempts because it preserves the ergonomics of past single function tools that either only provided suction or only provided irrigation but advantageously does so while providing both suction and irrigation. While the combination suction and irrigation tool is a vast improvement over prior attempts to produce such combination tools, improvements nonetheless remain desirable.

What is needed is an improved irrigation fluid delivery tool that also is well suited for use as a combination suction and irrigation tool.

SUMMARY

The present invention is directed to an irrigation fluid dispensing tool that is particularly well suited for manual, preferably one-handed, operation having a manipulable handgrip of a handle of the tool constructed and arranged to provide a flow controller capable of selective irrigation fluid flow control between at least a plurality of irrigation fluid flow control positions and preferably between at least a plurality of pairs, i.e., at least three, of irrigation fluid flow control positions. The irrigation fluid dispensing tool includes an irrigation fluid surge pump actuated by the flow controller when the flow controller is disposed in a surge fluid pump actuating position and an irrigation fluid flow obstructing valve actuated by the flow controller when the flow controller is disposed in an irrigation fluid flow obstructing position. A preferred irrigation fluid dispensing tool also has an irrigation fluid flow initiating position when the flow controller is disposed in an intermediate position between the surge flow actuating position and flow obstructing position.

When the flow controller is disposed in the irrigation fluid flow initiating position, a baseline flow of irrigation fluid is discharged from the tool. When the flow controller is disposed in the surge flow actuating position, squeezing of the handle causes the surge flow pump to discharge irrigation fluid from the tool at a flow rate of at least a plurality of times the baseline irrigation fluid flow rate preferably proportional to the amount of squeezing pressure applied by the user to the manipulable handgrip and flow controller in actuating surge flow. When the controller is disposed in the flow obstructing actuation position, the flow rate of irrigation fluid discharged from the tool is reduced below the baseline flow rate with flow of irrigation fluid discharge from the tool being completely stopped if desired. A preferred irrigation fluid dispensing tool preferably is configured with an automatic return that automatically returns or automatically displaces the flow controller back to the intermediate irrigation fluid flow initiating position from the surge flow actuating position as well as from the flow obstructing actuating position. Automatic return preferably is provided by the squeeze bulb acting as a spring captured in compression between the flow controller, preferably the squeeze handle lever, and the frame that urges the flow controller, preferably the squeeze handle lever, back toward the irrigation fluid flow initiating position.

In one preferred embodiment, the flow obstructing valve is a pinch valve enabling flow of irrigation fluid discharged out the tool to be reduced below the baseline flow rate and preferably stopped depending upon the amount of squeezing pressure applied by the user to the manipulable handgrip and flow controller in actuating the flow obstructing pinch valve.

A preferred irrigation fluid dispensing tool has an irrigation fluid surge flow pump formed of the flow controller, irrigation fluid reservoir having a compressible irrigation fluid holding chamber, and substantially rigid frame carrying the flow controller and irrigation reservoir. A preferred irrigation fluid reservoir is an elastomeric squeeze bulb mounted between a pair of spaced apart anchor arms of the frame with the flow controller mounted to one of the anchor arms enabling displacement of the flow controller relative to the reservoir and flow obstructing valve between the surge flow actuating position and flow obstructing actuating position by a user grasping the handle and manipulating the handgrip preferably via squeezing the handle.

A preferred flow controller is an elongate longitudinally extending concave curved squeeze handle lever having a lever arm with an elongate curved surge flow pump actuator section extending in one direction from the anchor arm to which the handle lever is mounted alongside the irrigation reservoir and an elongate irrigation fluid flow obstructing actuator section extending in an opposite direction from the anchor arm to or adjacent the flow obstructing valve. A preferred surge flow pump is a constant pressure displacement surge flow pump provided by a concave curved squeeze bulb actuating surface of the frame and the concave curved surge flow pump actuator section of the handle lever providing substantially constant pressure relative to displacement or compression of the squeeze bulb during squeezing of the manipulable handgrip by a user actuating surge fluid flow. In a preferred embodiment, the surge flow pump actuator section of the handle lever has a concave longitudinally curved surface facing the squeeze bulb generally conforming to a convex longitudinally curved sidewall of the bulb. The curved surface of the surge flow pump actuator section of the handle lever facing the bulb preferably is also concave in a transversely extending direction generally conforming to the radial or circumferential curvature of the bulb sidewall.

The squeeze handle lever preferably includes a mounting tab in the form of a pivot fulcrum received in a socket formed in the anchor arm enabling the squeeze handle lever to be pivotably mounted to the anchor arm in a manner where the handle lever can be pivotally displaced between the surge flow pump actuating position, the flow obstructing valve actuating position and the intermediate irrigation flow initiating position. A preferred fulcrum and socket construction enables the squeeze handle lever to be attached during tool assembly to the frame of the tool in a shipping or storage position where the handle lever not only can shield and protect the irrigation reservoir but also minimizes and preferably prevents potentially damaging contact therebetween during shipping and storage. Such a preferred fulcrum and socket construction enables the handle lever to be urged from the shipping or storage position toward the irrigation reservoir and frame into an operating position enabling the handle lever to pivot about the fulcrum between the surge flow pump actuating position, the flow obstructing valve actuating position and the intermediate irrigation flow initiating position.

In a preferred embodiment, the fulcrum has a pair of flexible detent snap arms each having oppositely outwardly extending detents that enable the fulcrum to be inserted into the anchor arm socket and initially snapped into the shipping and storage position during tool assembly before being snapped into the pivotable operating position when it is desired to use the tool. The socket formed in the anchor arm preferably is elongate and has shipping and storage position pockets adjacent an opening or mouth of the socket that releasably receives and retains the detents of the snap arms when the fulcrum is initially inserted into the socket during tool assembly. The socket includes operating position pockets which preferably are pivot journals separated from the shipping and storage position pockets by a shoulder over which the detents cam when the fulcrum is urged farther into the socket snapping the detents into place in the journals positioning the hand lever in the pivoting operating position. When disposed in the pivoting operating position, each detent of each snap arm becomes a pivot pin collectively forming a pivot about which the hand lever is pivotally displaced during tool operation.

In a preferred embodiment, the tool is equipped with suction and configured as a combination suction and irrigation tool having suction and irrigation fluid conduits or lines.

In a preferred combination suction and irrigation tool embodiment, tool has an elongate downwardly curved wand with a suction tip that is axially outwardly offset from and vertically offset above an irrigation fluid discharge tip disposed underneath the suction tip that is configured to direct irrigation fluid flow downwardly away from suction flow. This enables the suction tip to make first contact with a desired area and prevents discharged irrigation fluid from being sucked back into the suction tip without the fluid first irrigating the desired area.

These and other objects, features and advantages of this invention will become apparent from the following detailed description of the invention and accompanying drawings.

DRAWING DESCRIPTION

One or more preferred exemplary embodiments of the invention are illustrated in the accompanying drawings in which like reference numerals represent like parts throughout and in which:

FIG. 5 is a rear perspective view of the tool with the squeeze bulb removed;

FIG. 6 is a rear elevation view of the tool with the squeeze bulb removed and the frame shown in phantom depicting pivotable engagement of an irrigation flow controlling squeeze handle lever manipulable by a user grasping the tool to control discharge of irrigation fluid out the tool;

FIG. 7 is a rear fragmentary cross-sectional view of the tool with the squeeze bulb removed illustrating in more detail assembly of the squeeze handle lever to the frame of the tool;

FIG. 8 is an enlarged fragmentary perspective view of a squeeze handle lever anchor arm of the tool frame illustrating a handle lever mounting socket configured to enable mounting of the squeeze handle in one of a storage position and irrigation fluid tool operating position;

Figure 13:
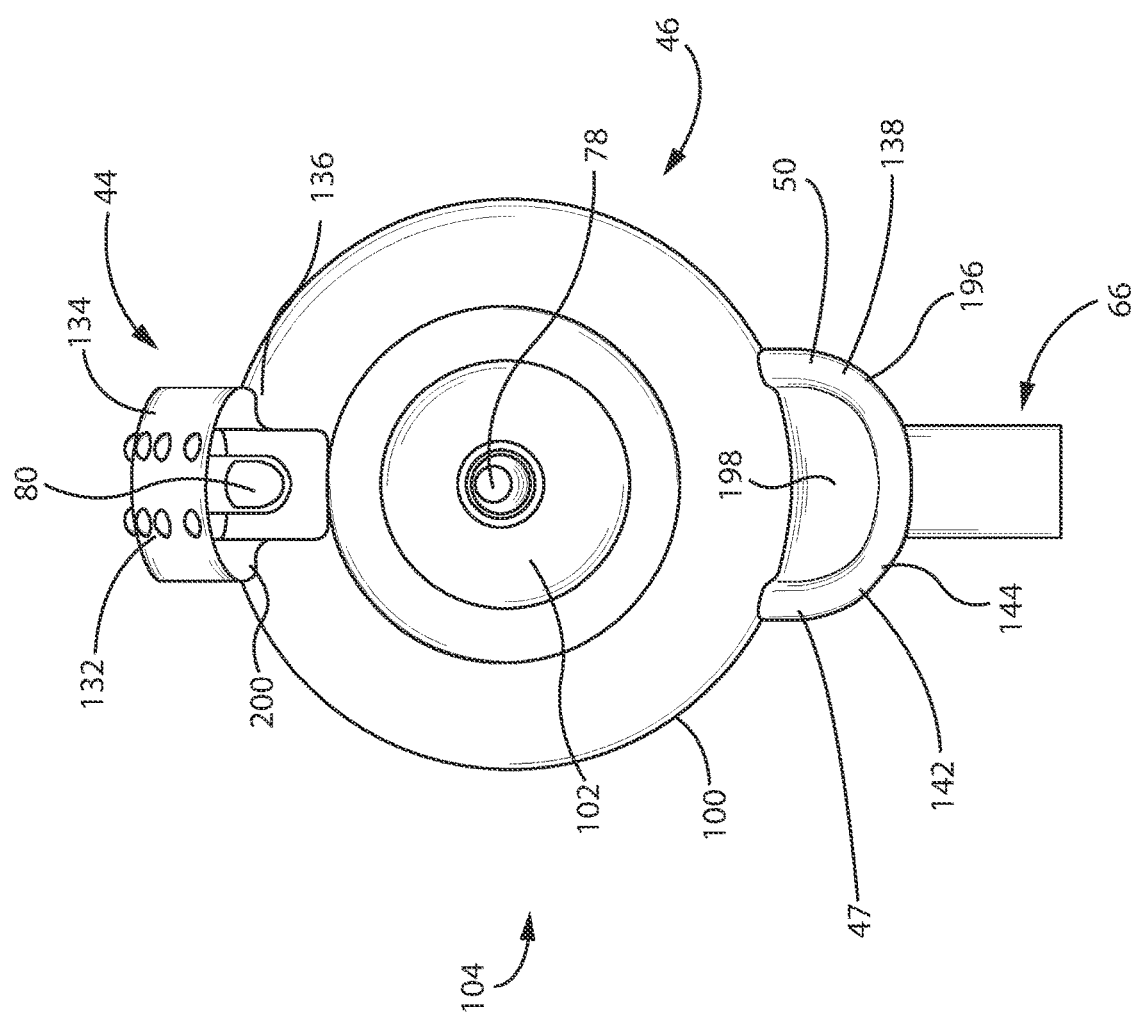
Figure 14:
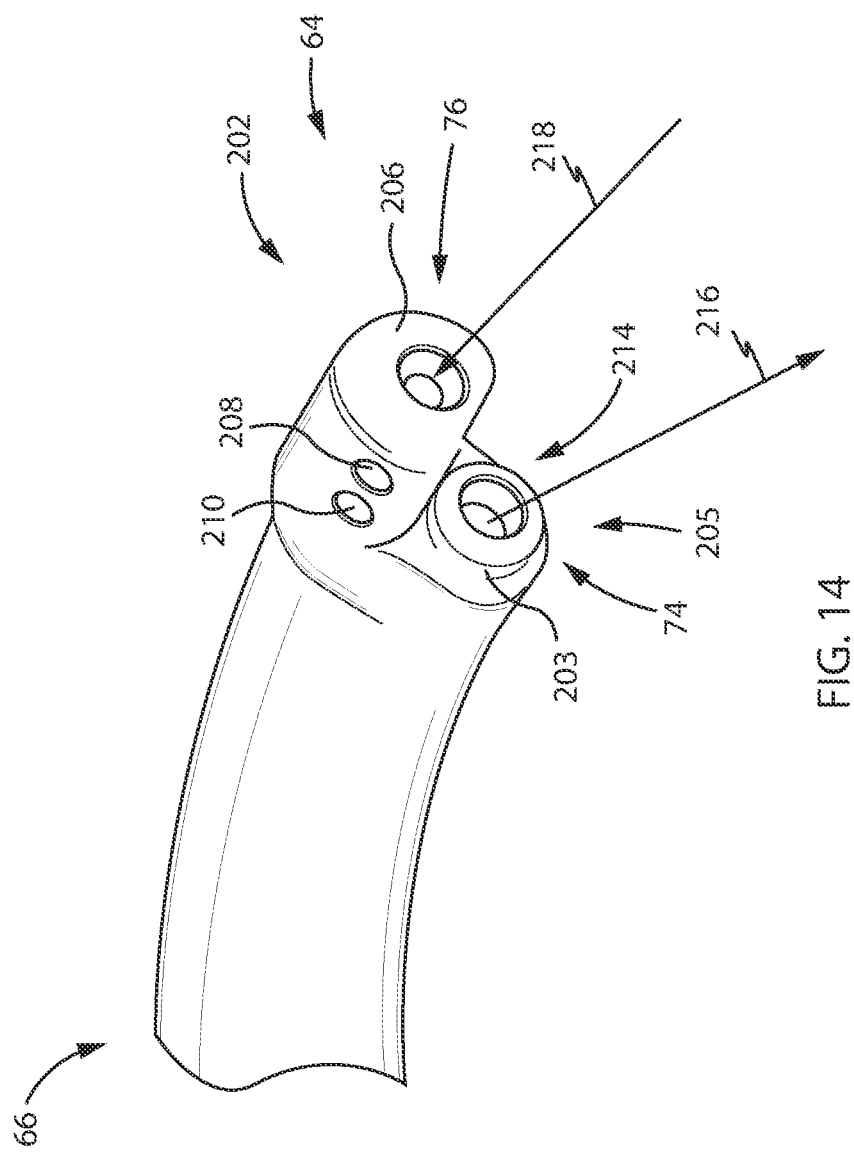

FIG. 13 is a rear sectional elevation view of the tool with a cross-section taken through the squeeze bulb rearwardly of the squeeze hand lever illustrating a concave transverse curvature of a surge flow pump actuator of the hand lever generally conforming to a curved outer radial or circumferential surface of the squeeze bulb; and FIG. 14 is an enlarged fragmentary perspective view of an end or tip of a wand of the tool depicting a preferred suction tip and irrigation fluid discharge tip configuration.

Before explaining one or more embodiments of the invention in detail, it is to be understood that the invention is not limited in its application the details of construction and the arrangement of the components set forth in the following description or illustrated in the drawings. The invention is capable of other embodiments, which can be practiced or carried out in various ways. Also, it is to be understood that the phraseology and terminology employed herein is for the puse of description and should not be regarded as limiting.

DETAILED DESCRIPTION

With reference to FIGS. 1-14, the present invention is directed to an irrigation fluid dispensing tool 40 that is well suited for medical and dental applications and which is particularly well suited for hand-held operation, preferably one-handed self-powered operation, during use. A preferred irrigation fluid dispensing tool 40 can be configured to include suctioning capability producing a combination suction and irrigation tool 42, such as is depicted in FIGS. 1-14, when so configured. Such a preferred tool 40, even when configured as a combination suction and irrigation tool 42, is self-powered by a user as it is operated without any electrical power preferably instead being operated by manual manipulation of the tool by one hand of the user while grasping the tool.

Whether equipped with suctioning capability and configured as a combination irrigation and suction tool 42, the irrigation fluid dispensing tool 40 of the present invention has a frame 44 that carries an irrigation fluid reservoir 46 and includes a manipulable hand grip 48 with a flow controller 50 displaceable during hand grip manipulation advantageously providing the ability to widely vary the flow of irrigation fluid 52 discharged from the tool 40 anywhere from a surge of fluid, a steady stream of fluid, a trickle of fluid, drops of fluid, to cessation of fluid flow. The manipulable handgrip 48 preferably includes a handrest 54 formed of part of the frame 44 that is disposed opposite the flow controller 50 capturing the reservoir 46 therebetween forming a handle 56 of the tool 40 that is grasped by a user during tool use. The handle 56 preferably includes the handrest 54, manipulable handgrip 48, and can and preferably also does include the reservoir 46.

The manipulable handgrip 48 is constructed and arranged to enable a user of the tool 40 grasping the handle 56 with one hand using a grip, such as a golf grip, pencil grip, or the like, to not only maneuver the tool 40 using one hand but also controllably manipulate the handgrip 48 using the same hand to start, stop and relatively precisely vary the rate of flow of irrigation fluid 52 discharged from the tool 40. Where the tool is equipped with suction and configured as a combination suction and irrigation tool 42, the same hand can also substantially simultaneously operate suction, including while gripping the handle 56, even while manipulating the handgrip 48 to control irrigation fluid flow.

The flow controller 50 is displaceable by manipulation of the hand grip 48 relative to one or both of the frame 44 and reservoir 46 between one of a plurality of irrigation fluid flow controlling positions that preferably includes at least one irrigation fluid discharge position causing irrigation fluid flow and an irrigation fluid flow obstructing position opposing irrigation fluid flow. The flow controller 50 preferably is displaceable in one of a plurality of irrigation fluid discharge positions that enable the rate of flow of irrigation fluid 52 discharged from the tool 40 to be controllably varied based on applied pressure, e.g., squeezing pressure, during handgrip manipulation. When manipulation of the handgrip 48 displaces the flow controller 50 in an irrigation fluid flow obstructing position, the flow controller 50 actuates a flow obstructing valve 58 that opposes flow of irrigation fluid 52 from the tool 40 preferably substantially completely blocking flow thereby preventing irrigation fluid discharge. As discussed in more detail below, a preferred flow obstructing valve 58 is a pinch-type valve or pinch valve 60.

When the flow controller 50 is disposed in one fluid discharge position, preferably a flow initiating position, at least some flow of irrigation fluid 52 is discharged from the tool 40 at a baseline irrigation fluid flow rate. When the flow controller 50 is disposed in another fluid discharge position, preferably a surge flow discharge position, the flow controller 50 actuates a surge flow pump 47 that causes irrigation fluid 52 from the reservoir 46 to be discharged from the tool 40 at a discharge flow rate greater than the baseline flow rate. Operation of the flow controller 50 can be regulated by one-handed manipulation of the handgrip 48 to vary irrigation flow rate from a surge discharge flow rate that is not only greater than the baseline flow rate but which can be surged to achieve discharge flow rates twice, three times, or even four times the baseline flow rate for at least a plurality of seconds, preferably at least a plurality of pairs, i.e., at least three, of seconds of substantially continuous irrigation fluid discharge from the tool 40.

An irrigation fluid dispensing tool 40 constructed in accordance with the present invention is elongate having a coupling end 62 at one end of the tool 40, a discharge end 64 at an opposite or free end of the tool 40, an irrigation fluid reservoir 46 disposed therebetween that accumulates and holds a supply of irrigation fluid ready for on-demand discharge when the flow controller 50 is actuated, a handle 56 formed of the manipulable handgrip 48 that includes handrest 54, reservoir 46 and flow controller 50 in operable cooperation with one another enabling a user grasping the handle 56 during tool use to manipulate the handgrip 48 to irrigate a desired area with irrigation fluid 52, and an elongate wand 66 extending from the handle 56 terminating at the tool discharge end 64. The flow controller 50 not only enables relatively precise control of irrigation fluid flow discharged out the tool 40, at least part of the flow controller 50 can also serve as a protective reservoir guard 68 that protects one or more parts of the tool 40, including the reservoir 46, after assembly including during packaging, shipment and storage of the tool 40 prior to tool use. Where the flow controller 50 also functions as a protective reservoir guard 68, it is at least initially disposed in a reservoir shielding position, e.g., shipping and storage position, which not only helps protect the reservoir 46 but also helps prevent contact with the reservoir 46 prior to tool use from adversely affecting operability of the reservoir 46 during tool use.

Figure 1:
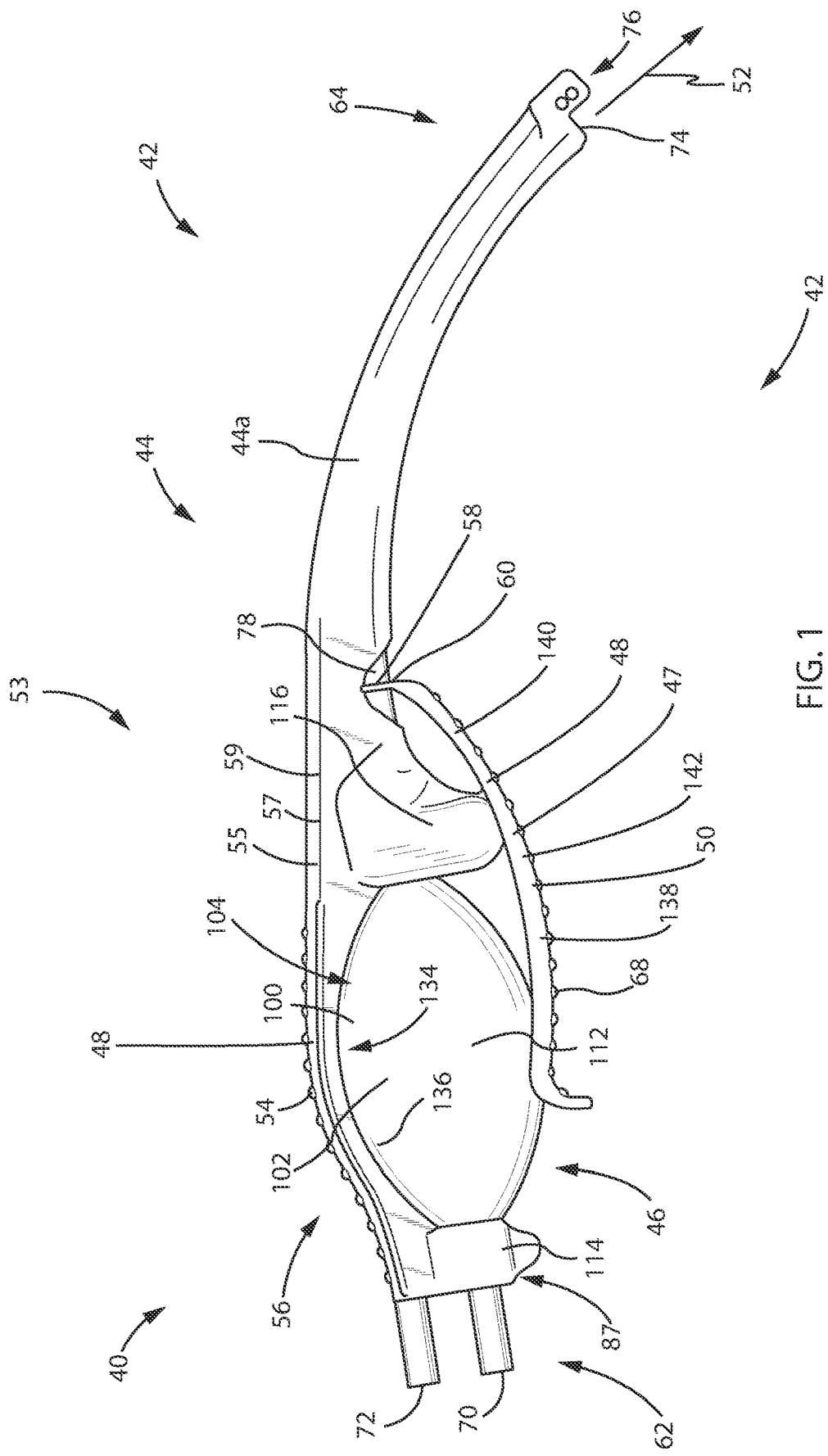
FIG. 1 is a side elevation view of an irrigation fluid dispensing tool of the present invention configured as combination suction and irrigation tool.
Figure 2:
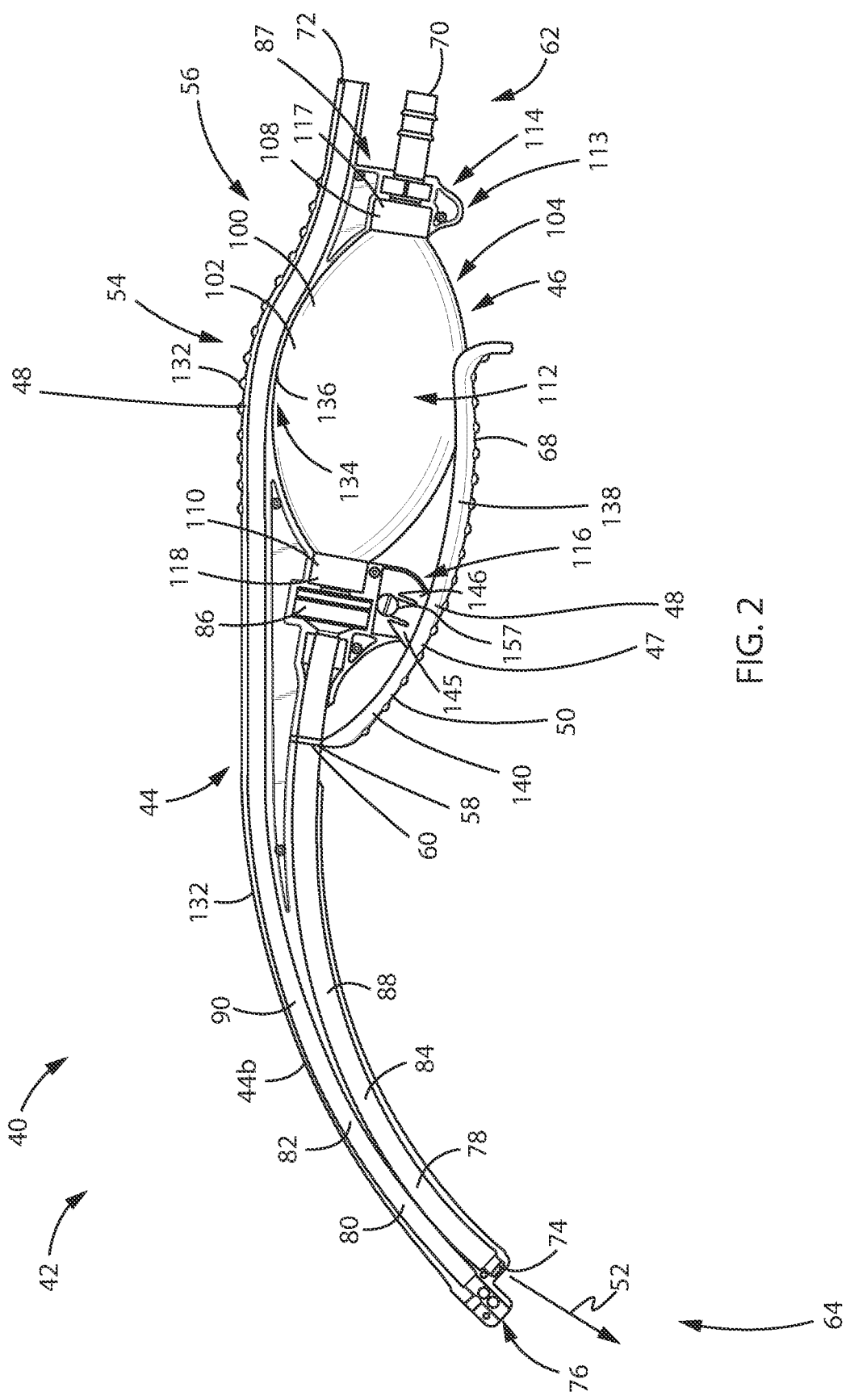
FIG. 2 is a side elevation view of the irrigation fluid dispensing tool with part of a frame of the tool removed illustrating irrigation and suction fluid conveying circuits housed within the tool frame.
Figure 3:
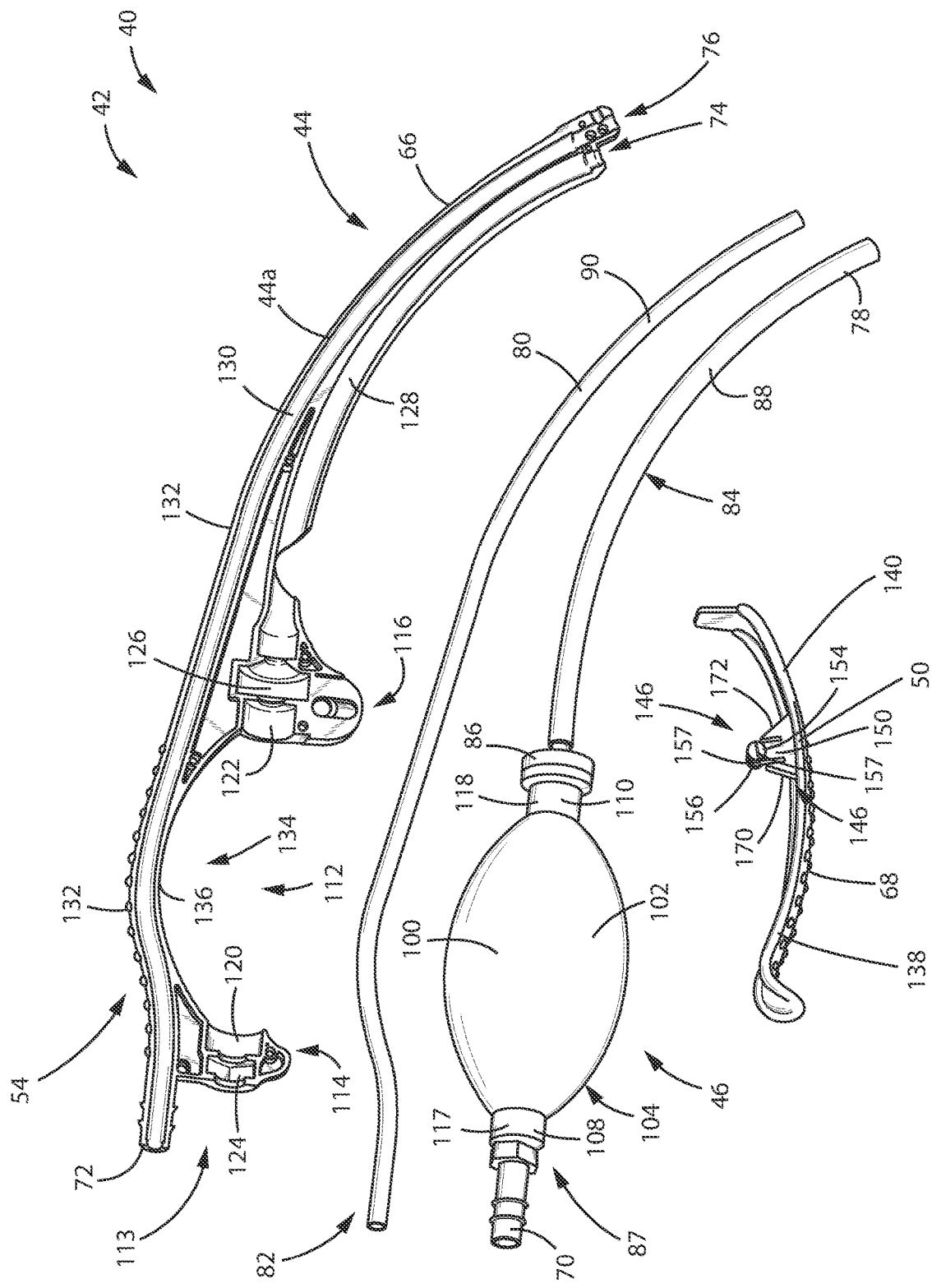
FIG. 3 is an exploded side elevation view of the tool.

The tool 40 not only includes the reservoir 46, flow controller 50 and flow-obstructing valve 58, but also includes at least one and preferably a plurality of fluid couplings 70, 72 disposed at the coupling end 62 of the tool 40, at least one and preferably a plurality of fluid ports 74, 76 disposed at the discharge end 64 of the tool 40, and, as best shown in FIGS. 2 and 3, at least one and preferably a plurality of fluid conduits 78, 80 disposed between the opposite ends 62, 64 of the tool 40. Where the tool 40 is a combination suction and irrigation tool 42 equipped with suctioning capability, the suction coupling 72, suction conduit 80, and suction inlet port 76 collectively form a suction fluid circuit 82 extending substantially the length of tool 40, 42 preferably extending substantially the length of the frame 44. Where the tool is equipped with suction and configured as a combination irrigation and suction tool 42, the same hand can also substantially simultaneously selectively vary suction flow by manually engaging a suction flow controller 53, such as is depicted in FIG. 1, which can be formed of a plurality of spaced apart suction vents 55, 57, and/or 59, formed in the frame 44 that are each in fluid flow communication with the suction conduit 80.

The irrigation fluid inlet coupling 70, irrigation fluid reservoir 46, irrigation fluid conduit 78, and irrigation fluid discharge port 74 collectively form an irrigation fluid circuit 84 extending substantially the length of the tool 40 and frame 44. Where the tool 40 is equipped with an irrigation fluid flow obstructing valve 58, the irrigation fluid circuit 84 not only includes the valve 58, but the circuit 84 can also and preferably does include a check valve 86, e.g., one-way flow valve, disposed downstream from the reservoir 46 and upstream of valve 58 to prevent irrigation fluid 52 in the irrigation fluid conduit 78 downstream of the reservoir 46 from back-flowing into the reservoir 46. The circuit 84 preferably also includes another one-way flow valve 87 or check valve 87 disposed upstream of the reservoir 46, e.g., squeeze bulb 104. Where the flow obstructing valve 58 is a pinch valve 60, the irrigation fluid circuit 84 preferably includes such a check valve 86 to prevent irrigation fluid 52 in the section of irrigation fluid conduit 78 between the pinch valve 60 and reservoir 46 from back-flowing into the reservoir 46. This arrangement also advantageously prevents air from being sucked into the reservoir 46 when the flow obstructing valve 58 is a pinch valve 60 that is being actuated before the pinch valve 60 is fully actuated and substantially completely sealed blocking irrigation fluid flow through the valve 60. If desired, the check valve 86 need not be a component separate from the reservoir 46 as the reservoir 46 can include the check valve 86 such as by being integrally formed as part of the reservoir 46.

Where the reservoir 46 is a squeeze bulb 104 and the flow obstructing valve 48 is a pinch valve 60, the combination of an irrigation fluid circuit 84 having a check valve 87 upstream of the squeeze bulb 104, check valve 86 downstream of the squeeze bulb 104 and pinch valve 60, enables the squeeze bulb 104 to function as a suction pump after being compressed during surge fluid discharge and then allowed to de-compress more rapidly sucking irrigation fluid through check valve 87 and the squeeze bulb inlet 108 in the squeeze bulb 104 replenishing the squeeze bulb 104 as the shape memory of the squeeze bulb sidewall 100 returns the squeeze bulb 104 back to its uncompressed state. This advantageously more quickly replenishes the squeeze bulb 104 with a full charge of irrigation fluid 52 thereby more rapidly readying the squeeze bulb 104 for surge fluid discharge.

The irrigation fluid reservoir 46 holds enough irrigation fluid 52 for a user of the tool 40 to surge or rapidly increase flow of irrigation fluid 52 discharged from the tool 40 when the flow controller 50 is actuated. The reservoir 46 has a curved sidewall 100 defining a longitudinally extending elongate bulbous, generally oval, e.g., egg-shaped, irrigation fluid-holding chamber 102 having a width or diameter greater than a width or diameter of the irrigation fluid conduit 78 producing a reservoir 46 that holds at least a plurality of times the volume of irrigation fluid 52 than held the rest of the irrigation fluid circuit 84, e.g., irrigation fluid conduit 78, thereby enabling the reservoir 46 to provide sufficient irrigation fluid 52 to surge or rapidly increase irrigation fluid flow discharged from the tool 40 when surge flow is actuated.

A preferred reservoir 46 has a flexible sidewall 100 producing a compressible irrigation fluid-holding chamber 102 in operable cooperation with the flow controller 50 defining a surge flow pump 47 when surge flow is actuated by the flow controller 50 from user manipulation, e.g., squeezing, of the handgrip 48. One preferred reservoir embodiment is an elastomeric squeeze bulb 104 formed by a flexible, resilient and elastomeric sidewall 100 defining a bulbous or generally oval, e.g. egg-shaped, compressible irrigation fluid-holding chamber 102 having an irrigation fluid inlet 108 at one end and an irrigation fluid outlet 110 at an opposite end. In a preferred embodiment, the squeeze bulb 104 holds about 2.25 ounces of irrigation fluid 52, which is at least a plurality of times greater than an approximately one ounce of irrigation fluid 52 disposed in the rest of the irrigation fluid circuit 84, advantageously enabling a surge of irrigation fluid 52 to be forcibly expelled, e.g., pumped, from the bulb 104 when the manipulable handgrip 48 is squeezed causing a corresponding surge of irrigation fluid 52 to be discharged from the tool 40.

Where the tool 40 includes an irrigation fluid flow obstructing valve 58 of pinch-type valve construction, e.g., pinch valve 60, at least the portion of the irrigation fluid conduit 78 in operable cooperation therewith is formed of an elongate substantially liquid-tight tube 88, e.g., section of elastomeric tubing, disposed in the region of the valve 60 that is flexible, e.g., collapsible, and thereby capable of being pinched substantially closed during pinch valve operation. Where the frame 44 is formed of a plurality of pieces or halves 44a, 44b that snap together to form the frame 44, at least the portion of the irrigation fluid conduit 78 extending downstream of the check valve 86 can be and preferably is formed of an elongate flexible tube 88 that preferably is of elastomeric construction, e.g., rubber, silicone, nylon, polyurethane, PVC or polyethylene tubing. Where the frame 44 is of multiple piece construction, e.g., snap together construction, the suction fluid conduit 82 preferably also is formed of an elongate tube 90, which can also be flexible and of elastomeric construction. Where the frame 44 is of substantially gas-tight and liquid-tight construction, one or both fluid conveying conduits 78, 80 can be integrally formed within the frame 44 which can eliminate the need for one or both corresponding fluid conveying tubes 88, 90.

As best shown in FIG. 3, the frame 44 has a reservoir receptacle 112 that includes a reservoir mount 113 formed by a pair of spaced apart reservoir anchor arms 114, 116 that engage opposite ends of the reservoir 46 capturing the reservoir therebetween mounting the reservoir to the frame 44. Where the reservoir 46 is a squeeze bulb 104, the generally cylindrical outwardly projecting bulb inlet 108 and bulb outlet 110 respectively provide squeeze bulb mounting trunnions 117, 118 that are received in a corresponding one of a pair of spaced apart generally coaxial sockets 120, 122 formed in a respective one of the anchor arms 114, 116 in mounting the squeeze bulb 104 to the frame 44. If desired, each anchor arm 114, 116 can include or otherwise carry a reservoir anchor in the form of an outward projection, such as a fluid coupling, e.g., nipple, which couples with a corresponding inlet 108 and outlet 110 of the bulb 104, such as by being telescopically received in the corresponding inlet 108 and outlet 110. Other reservoir mounting arrangements are contemplated as being within the scope of the present invention.

The frame 44 preferably further secures the reservoir 46 to the frame 44 by fixturing the irrigation fluid inlet coupling 70 extending from the bulb inlet 108 to one reservoir anchor arm, e.g., inlet end anchor arm 114, and by fixturing the check valve 86 extending from the bulb outlet 110 to the other reservoir anchor arm, e.g., outlet end anchor arm 116. As is best shown in FIG. 3, the inlet end anchor arm 114 has a coupling seat 124 that receives, locates, and secures coupling 70 thereto helping further anchor the inlet end of the reservoir 46, preferably bulb inlet 108, to the frame 44. The outlet end anchor arm 116 has a valve seat 126 that receives, locates, and secures the check valve 86 within the arm 116 thereby helping further anchor the outlet end of the reservoir 46, preferably bulb outlet 110, to the frame 44.

With continued reference to FIG. 3, the frame 44 seats the irrigation fluid tube 88 in an elongate longitudinally extending irrigation fluid tubing seating channel 128 formed in each half 44a, 44b that extends from the check valve seat 126 along substantially the entire length of the wand 66 to or adjacent the irrigation fluid discharge port 74. Where the tool 40 includes suctioning capability, the suction fluid tube 90 seats in an elongate longitudinally extending suction fluid tubing seating channel 130 formed in each frame half 44a, 44b that extends substantially the entire length of the tool 40 from or adjacent the suction fluid coupling 72 at one end to or adjacent the suction intake port 76 at the opposite end. When both frame halves 44a, 44b are assembled together, the mated irrigation fluid tubing seating channels 128 and the suction fluid tubing seating channels 130 form generally cylindrical elongate conduits within the assembled frame 44.

When both halves 44a, 44b of the frame 44 are assembled together, the irrigation fluid inlet coupling 70 and check valve 86 are captured between the frame halves 44a, 44b fixturing them in place thereby anchoring them and the reservoir 46, e.g., squeeze bulb 104, to the frame 44. The check valve 86 preferably also is substantially completely enclosed within outlet end anchor arm 116 such that the assembled frame 44 not only hides the valve 86 within the arm 116 but also protects the valve 86. When both halves 44a, 44b are snapped together to form assembled frame 44, the irrigation fluid tube 88 is captured between the frame halves 44a, 44b substantially completely disposing the tube 88 within the frame 44 such that the frame 44 protects and substantially completely hides the tube 88. Where the tool 40 is equipped with suction, the suction fluid tube 90 also is likewise substantially completely hidden within and protected by the frame 44.

The tool 40 has an elongate backbone 132 that preferably extends along a dorsal, e.g., upwardly facing, side of the frame 44 that extends substantially the length of the tool handle 56 and which preferably extends substantially the length of the tool 40. The handrest 54 is formed of part of the backbone 132 disposed adjacent the coupling end 62 of the tool 40 that extends alongside the reservoir 46, e.g., squeeze bulb 104, providing a substantially rigid reservoir support 134 having a surge flow actuating surface 136 against which one side of the reservoir 46, e.g., squeeze bulb 104, is disposed, e.g., adjoins or abuts. Actuating surface 136 is elongate and has a curvature in a lengthwise direction that substantially complementarily conforms to the curvature of the curved sidewall 100 of the reservoir 46, e.g., squeeze bulb 104, which more uniformly distributing forces experienced by the reservoir 46 during surge flow.

The flow controller 50 is operatively connected to the frame 44 and disposed in operable cooperation with the reservoir 46 such that manipulation of the hand grip 48 by a user grasping the tool handle 56 displacing the flow controller 50 relative to the reservoir 46 and/or relative to the frame 44 in one direction actuates the surge flow pump 47 expelling surge flow of irrigation fluid 52 from the reservoir 46 that is discharged from the tool 40 and in another direction to cease actuation stopping surge flow. The flow controller 50 preferably is displaced relative to the frame 44 and reservoir 46 toward the reservoir 46 to actuate the surge flow pump 47 and displaced relative to the frame 44 and reservoir 46 away from the reservoir 46 to cease actuation stopping surge flow.

The surge flow pump 46 preferably is formed by operable cooperation between the flow controller 50 and reservoir 46 with actuation occurring when the flow controller 50 is displaced toward the reservoir 46 to an irrigation fluid discharge position by manipulation of the handgrip 48 by a user operating the tool 40 squeezing or compressing the compressible irrigation-fluid chamber 102 expelling irrigation fluid 52 therefrom. In a preferred embodiment, the surge flow pump 47 is formed of the flow controller 50, reservoir 46, e.g., squeeze bulb 104, and reservoir receptacle 112, including the actuating surface 136 of the substantially rigid reservoir support 134 of the frame backbone 132 that extends along the hand rest 54 opposite the flow controller 50. During surge flow pump operation, displacement of the flow controller 50 towards the reservoir 46 by manipulation of the handgrip 48 actuates the pump 47 by squeezing or compressing the compressible chamber 102 against the actuating surface 136 of the rigid reservoir support 134 forcibly expelling irrigation fluid 52 from the chamber 102 causing a surge in the flow of irrigation fluid 52 discharged from the tool 40. Displacement of the flow controller 50 away from the reservoir 46 via handgrip manipulation ceases squeezing or compression of the reservoir chamber 102 de-actuating the pump 47 ceasing surge flow.

Where it is desired to substantially completely cease irrigation fluid flow out the tool 40, the handgrip 48 can be manipulated to displace the flow controller 50 into an irrigation fluid flow obstructing position that actuates flow obstructing valve 58 closing the valve 58. In a preferred embodiment, displacement of the flow controller 50 into an irrigation fluid flow obstructing position via handgrip manipulation displaces the flow controller 50 toward the flow obstructing valve 58 preferably actuating the valve 58 by engaging the valve 58 to cease irrigation fluid discharge. When it is desired to resume irrigation fluid flow, handgrip manipulation that displaces the flow controller 50 away from the valve 58 disengages the flow controller 50 from the valve 58 opening the valve 58.

In a preferred embodiment, the flow controller 50 is pivotally operatively connected to the frame 44 such that handgrip manipulation applying pressure to the flow controller causing pivoting displacement of the flow controller 50 in one direction toward the reservoir 46 actuates the surge flow pump 47 causing surge flow when the displaced flow controller 50 reaches a surge flow position, handgrip manipulation applying pressure to the flow controller 50 causing pivoting displacement of the flow controller 50 in an opposite direction actuates the flow obstructing valve 58 blocking flow when the displaced flow controller 50 reaches a flow obstructing position, and handgrip manipulation releasing pressure on the flow controller 50 causes the flow controller 50 to automatically return to an intermediate flow discharge position allowing baseline flow rate discharge of irrigation fluid from the tool 40. One or both the reservoir 46, e.g., squeeze bulb 104, and valve 58 functions as a flow controller biasing element that urges the flow controller 50 into returning to the intermediate flow discharge position when no pressure is applied to the flow controller 50. In a preferred embodiment, automatic return preferably is provided by the reservoir 46, preferably the squeeze bulb 104, acting as a spring captured in compression between the reservoir 46, preferably the squeeze bulb 104, and the flow controller 50, preferably the squeeze handle lever, and the frame 44 that urges the flow controller 50, preferably the squeeze handle lever, back toward the irrigation fluid flow initiating position.

In one preferred embodiment, the reservoir 46, e.g., squeeze bulb 104, is a biasing element that returns the flow controller 50 to the intermediate flow discharge position when the flow controller 50 is disposed in a surge flow position and pressure on the flow controller 50 is removed or released. In such a preferred embodiment, the flow obstructing valve 58 is a biasing element that returns the flow controller 50 to the intermediate flow discharge position when the flow controller 50 is disposed in a flow obstructing position and pressure on the flow controller 50 is removed or released.

In a preferred flow controller embodiment, the flow controller 50 has a surge fluid pump actuator 138 overlying or overlapping part of the reservoir 46 that actuates the surge fluid pump 47 by engaging and squeezing the compressible chamber 102 of the reservoir 46, e.g., compressing the squeeze bulb 104, when the flow controller 50 is pivoted toward the reservoir 46, e.g., squeeze bulb 104, displacing the surge fluid pump actuator 138 against the reservoir 46, e.g., squeeze bulb 104, thereby squeezing or compressing the reservoir 46, e.g., squeeze bulb 104. In such a preferred embodiment, the flow controller 50 has a flow obstructing valve actuator 140 spaced from the surge fluid pump actuator 138 that actuates flow obstructing valve 58 by engaging or pressing the valve 58 to close the valve 58 and obstruct irrigation fluid flow when the flow controller 50 is pivoted toward the valve 58. As previously discussed, a flow controller 50 of an irrigation fluid dispensing tool 40 of the present invention has an automatic baseline irrigation fluid discharge flow rate return as the flow controller 50 is biased into automatically pivoting, e.g., returning, back to the intermediate flow discharge position when the flow controller 50 is released or freed.

As discussed in more detail below, the flow controller 50 can be and preferably is initially attached to the frame 44 in a shipping or storage position where the flow controller 50 protects or shields at least one and preferably both the reservoir 46, e.g., squeeze bulb 104, and flow obstructing valve 58, e.g., pinch valve 60, prior to tool use. When the flow controller 50 is disposed in the protective shipping or storage position, the flow controller 50 serves as a protective guard 68 that shields and protects at least the reservoir 46, e.g., squeeze bulb 104, which preferably shields and protects both the reservoir 46, e.g., squeeze bulb 104, and valve 58, e.g., pinch valve 60. When the flow controller 50 is disposed in the protective shipping or storage position, the flow controller 50 preferably is spaced from the reservoir 46, e.g., squeeze bulb 104, preventing contact therewith thereby preventing the flow controller 50 from plastically deforming or otherwise damaging the reservoir 46, e.g., squeeze bulb 104, prior to tool use. When the flow controller 50 is disposed in the protective shipping or storage position, the flow controller 50 preferably also is spaced from the flow obstructing valve 58, preferably pinch valve 60, preventing contact therewith thereby preventing the flow controller 50 from plastically deforming or otherwise damaging any part of the valve 58 and/or 60.

When the flow controller 50 is disposed in the protective shipping or storage position, the flow controller 50 preferably is retained in the protective shipping or storage position until pressure is manually applied against the flow controller 50 sufficient to displace the flow controller 50 substantially simultaneously towards the reservoir 46, e.g., squeeze bulb 104 and valve 58, e.g., pinch valve 60, urging the flow controller 50 into an operating position where the flow controller 50 becomes pivotable. In a preferred embodiment, the flow controller 50 can be disposed in snap fit substantially immovable frictional engagement with the frame 44 substantially immovably fixing the flow controller 50 in place relative to the frame 44 in the protective shipping or storage position safely spacing the flow controller 50 from the reservoir 46, e.g., squeeze bulb 104, and/or valve 58, e.g. pinch valve 60, until displaced, e.g., snapped, farther toward the frame 44 and reservoir 46 into the operating position such that the flow controller 50 pivotally engages the frame 44 allowing pivotable relative movement therebetween during use and operation of the tool 40.

Figure 4:
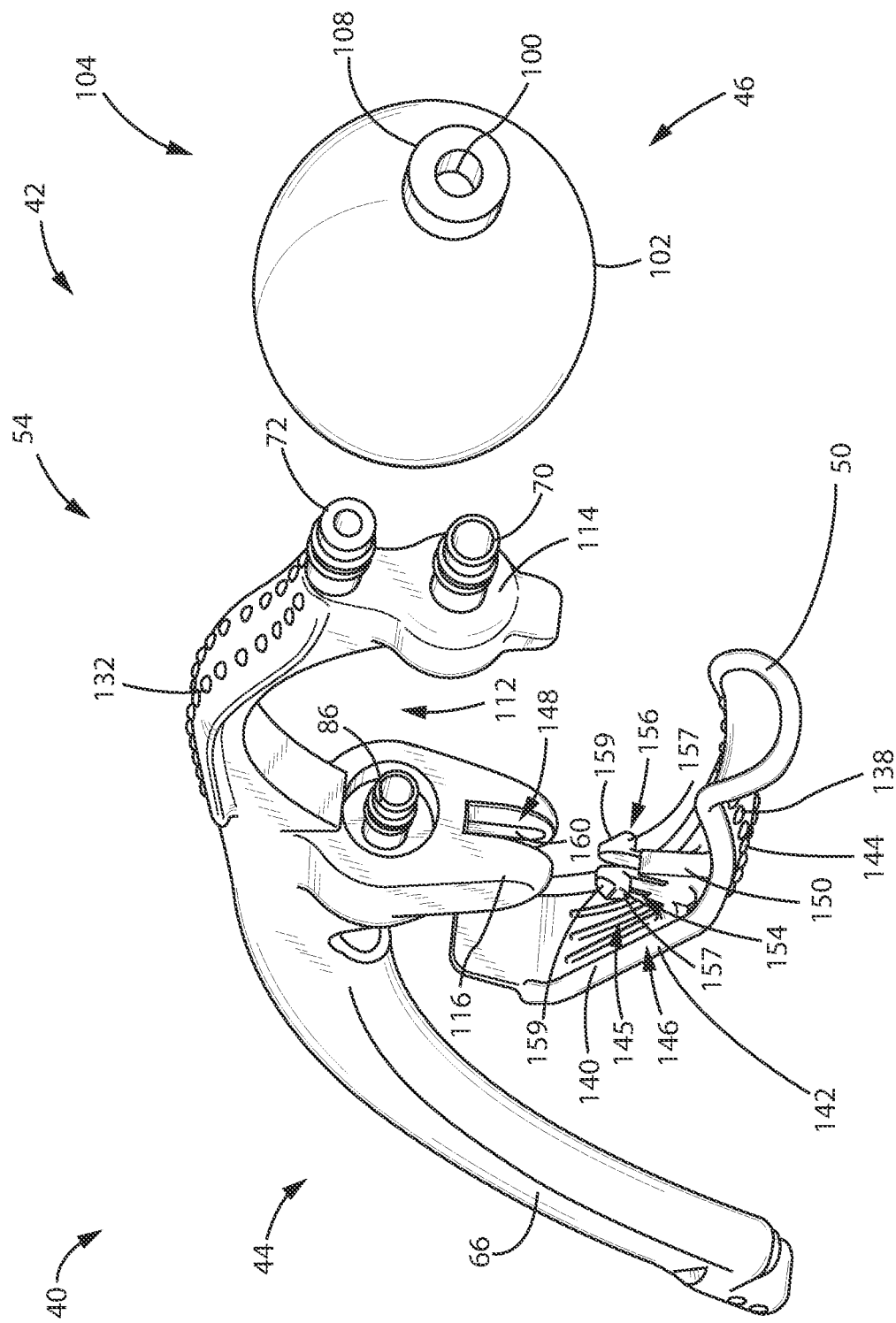
FIG. 4 is an exploded rear perspective view of the tool.
Figure 9:
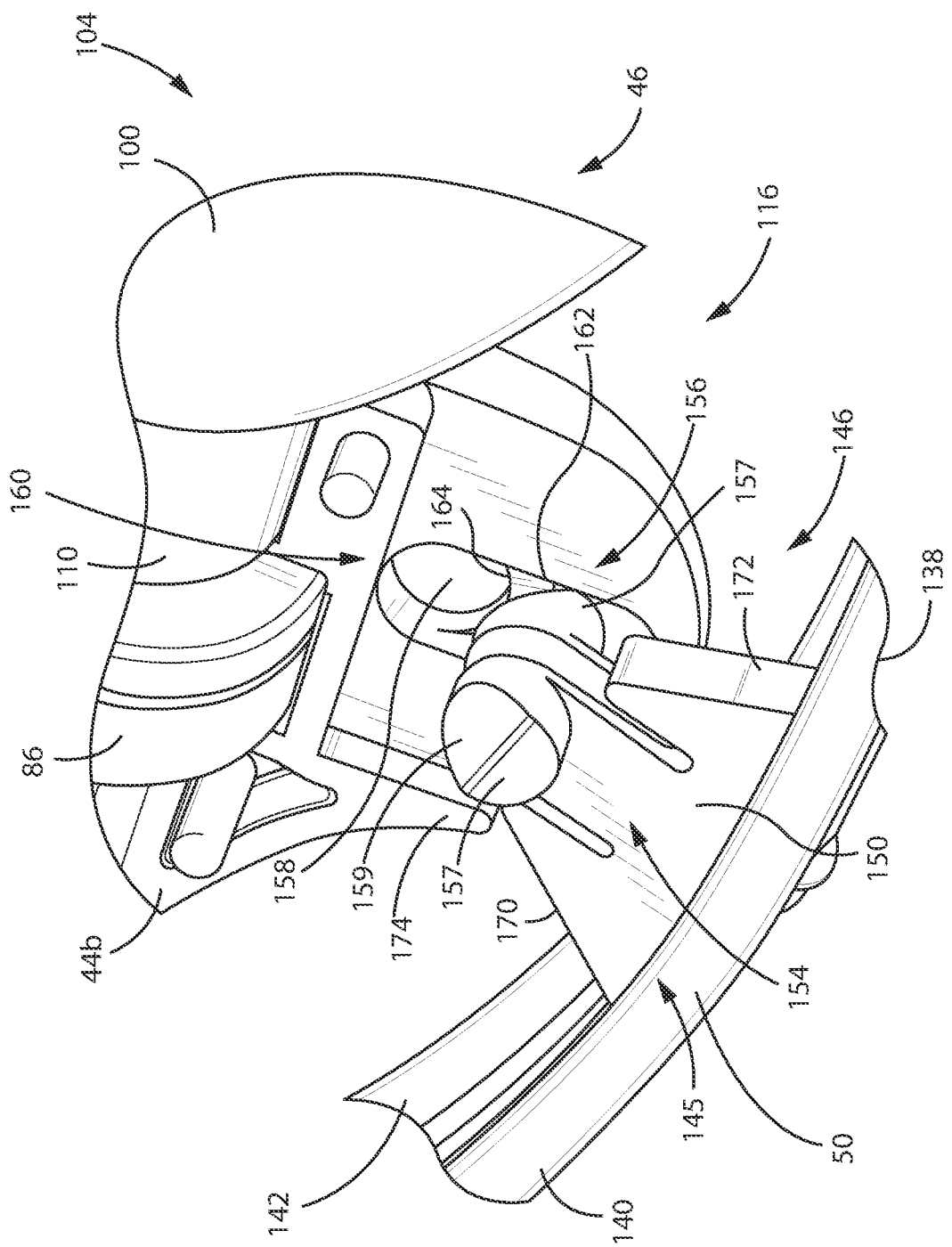
FIG. 9 is an enlarged fragmentary perspective view of the anchor arm of FIG. 8 showing a mounting tab of the squeeze handle lever mounted thereto in a shipping and storage position.

With continued reference to FIG. 3 and additional reference to FIGS. 4-6, a preferred flow controller 50 is a squeeze handle lever 142 extending longitudinally alongside the reservoir 46 generally parallel to the handrest 54 forming part of the manipulable handgrip 48 and tool handle 56. The handle lever 142 is an elongate lever arm 144 having a generally transversely projecting handle lever mounting tab 145 that preferably is a pivot fulcrum 146 used to mount the handle lever 142 to the frame 44. In attaching the handle lever 142 to the frame 44, the mounting tab 145, preferably fulcrum 146, is received in a handle lever mounting socket 148 that preferably is a cavity formed in a free or bottom end of the reservoir outlet anchor arm 116 of the frame 44.

With reference to FIGS. 1-2 and 5-6, the squeeze handle lever 142 is shown attached to the frame 44 of the tool 40 with the mounting tab 145, preferably fulcrum 146, received in mounting socket 148 and disposed in engagement with the mounting arm 116 of frame 44. With additional reference to FIG. 7, the mounting tab 145, preferably fulcrum 146, is formed of a generally triangular, e.g., generally pyramidal, base 150 having a pivot 152 at the free end of the fulcrum base 150 about which the handle lever 142 can pivot during tool operation when the handle lever 142 is mounted to the frame 44 and disposed in the flow controller operating position.

With additional reference to FIGS. 7-10, the pivot 152 of the fulcrum 146 preferably is formed of a pair of resiliently outwardly biased oppositely facing snap arm detents 154, 156 each having an outwardly extending generally round, e.g., generally cylindrical, pivot pin 157 received in a corresponding recessed generally cylindrical pocket that preferably is a pivot journal 158 at the end of a respective elongate fulcrum-receiving socket channel 160 formed in each frame half 44a, 44b, only one of which is shown in FIG. 8, in mounting the squeeze handle lever 142 to the mounting arm 116 of the frame 44 in the operating position. To facilitate insertion into the socket 148, each detent 154, 156 has a canted or angled leading edge 159 enabling each detent 154, 156, e.g., each pivot pin 157, to cam along a corresponding socket channel 160 until each detent 154, 156 snaps into its corresponding pivot journal 158. When each detent 154, 156 is received in a corresponding pivot journal 158, the handle lever 142 is pivotally mounted to the frame 44 in a manner permitting the handle lever 142 to rotate relative to the reservoir 46, e.g., squeeze bulb 104, and frame 44 in either direction about the pivot 152, e.g., pivot pins 157, formed by the detents 154, 156.

With continued reference to FIGS. 7-10, where the frame 44 of the tool 40 is configured to enable the handle lever 142 to be mounted to the frame 44 in a protective shipping or storage position, each socket channel 160 of each frame half 44a, 44b includes a storage position retainer seat or pocket p disposed between the entrance of the socket channel 160, e.g., mouth or opening of socket 148, and pivot journal 158. The storage position retainer pocket 162 is separated from the pivot journal 158 by an upraised beveled pivot retainer shoulder 164 formed in each socket channel 160 of each frame half 44a, 44b over which a corresponding detent 154, 156 cams when the handle lever 142 is urged from the storage position into the operating position.

During initial assembly, the mounting tab 145, preferably fulcrum 146, of the squeeze handle lever 142 is inserted into the mouth of the socket in the anchor arm 116 of the frame 44 with the canted leading edge 158 of each detent 154, 156 camming over a storage position retainer abutment 166 disposed at or adjacent the socket mouth snapping into the storage position retainer pocket 162 when the abutment 166 is cleared. When both detents 154, 156 are received in a corresponding storage position retainer pocket 162 of a respective frame half 44a, 44b, the handle lever 142 is retained in the storage position. When disposed in the storage position, opposite converging sides 170, 172 of the mounting tab 145, preferably fulcrum 146, serve as rotation limiters or stops that keeps the handle lever 142 suitably spaced from the reservoir 46, e.g., squeeze bulb 104, to protect it while preventing deformation and damage to it. Rotation or over-rotation of the of the hand lever 142 is prevented while in the storage position by abutment of a corresponding one of the fulcrum sides 170, 172, e.g., rotation stops, against a respective upraised stop 174 of the anchor arm 116.

With reference once again to FIGS. 1 and 2, when it is desired to use the tool 40, such as after removing the tool 40 from any package (not shown) in which the tool 40 was shipped, a user of the tool 40 urges the squeeze handle lever 142 towards the frame 44 causing the canted leading edge 158 of each detent 154, 156 of the mounting tab 145, preferably fulcrum 146, to cam over the pivot retainer shoulder 166 until each detent 154, 156 snaps into a respective pivot journal 158 of a corresponding frame half 44a, 44b. Manually pressing against the handle lever 142 thereby urges each 154, 156 from its respective storage position retainer pocket 162 into a corresponding pivot journal 158 enabling the handle lever 142 to rotate relative to the frame 44 and reservoir 46, e.g., squeeze bulb 104, when the handgrip 48 is grasped by the user and manipulated during tool use. When both detents 154, 156 are received in a corresponding pivot journal 158 of a respective frame half 44a, 44b, the handle lever 142 is pivotably retained in the operating position. When pivotally retained, the handle lever 142 can pivot relative to the frame 44 and reservoir 46, e.g., squeeze bulb 104, between the irrigation fluid surge flow pump actuating position and the irrigation flow obstructing valve actuating position.

With continued reference to FIGS. 1 and 2, during tool use and operation, a user grasps the manipulable handle 56 of the tool 40 and manipulates the handle 56 by squeezing the squeeze handle lever 142 in a manner that pivots or rotates the handle lever 142 about the fulcrum 146 relative to the frame 44 in one direction to actuate surge flow and pivots or rotates the handle lever 142 about the fulcrum 146 relative to the frame 44 in an opposite direction to obstruct discharge of irrigation fluid 52 from the tool 40. When the handle 56 is manipulated by squeezing the handle lever 142 in a manner that pivots or rotates the handle lever 142 toward the surge flow actuating position, the handle lever 142 is pivoted or rotated toward the reservoir 46, e.g. squeeze bulb 104, actuating the surge flow pump 47. When the handle 56 is manipulated by squeezing the handle lever 142 in a manner that pivots or rotates the handle lever 142 toward the irrigation fluid flow obstructing position, the handle lever 142 is pivoted or rotated toward the flow obstructing valve 58, e.g. pinch valve 60, actuating the valve 58.

Pinch Valve Construction and Operation

Figure 10:
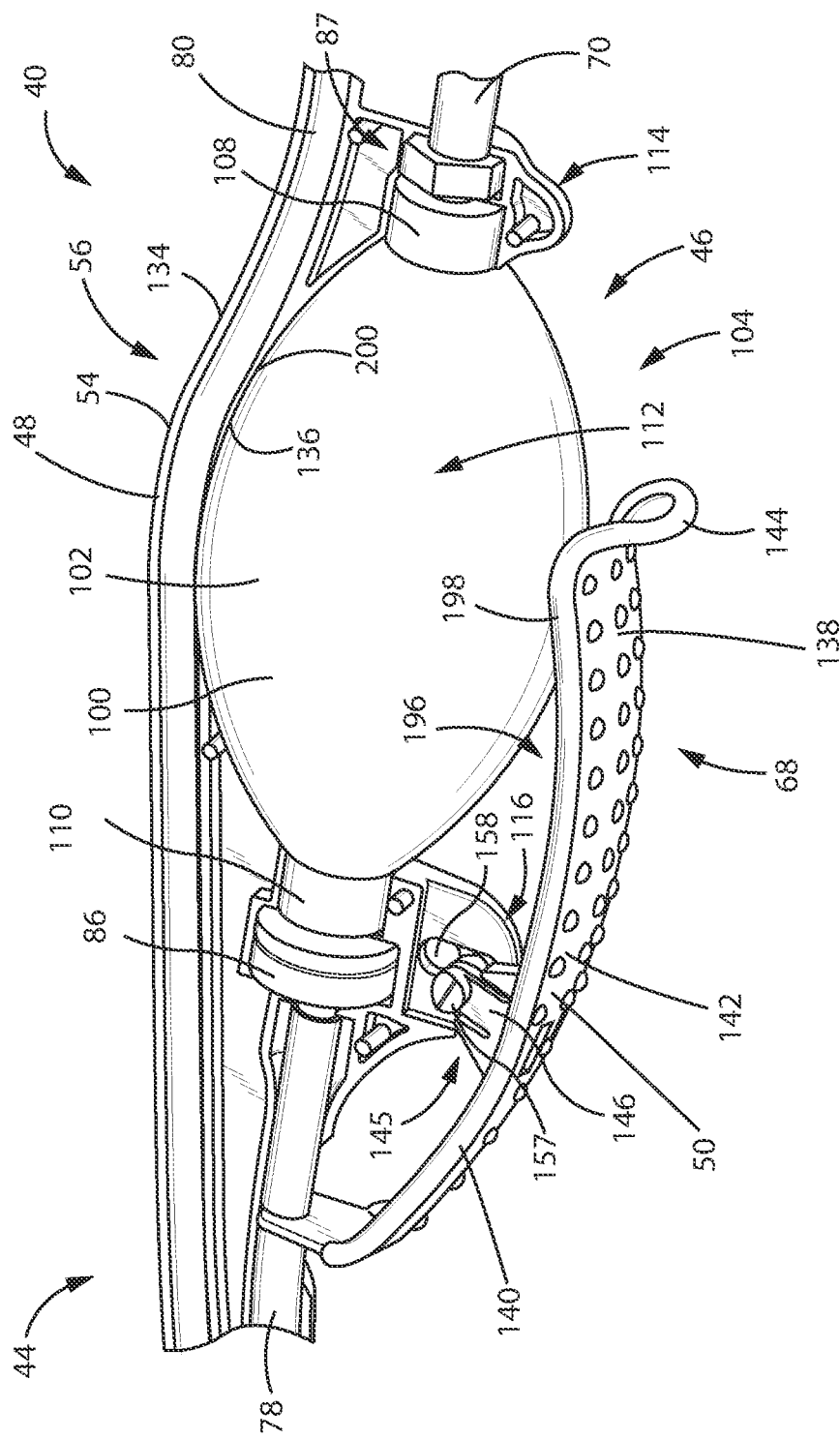
FIG. 10 is a fragmentary side perspective view of the tool with a portion of the frame removed showing the squeeze handle lever mounted to the anchor arm of the frame in the shipping and storage position.
Figure 11:
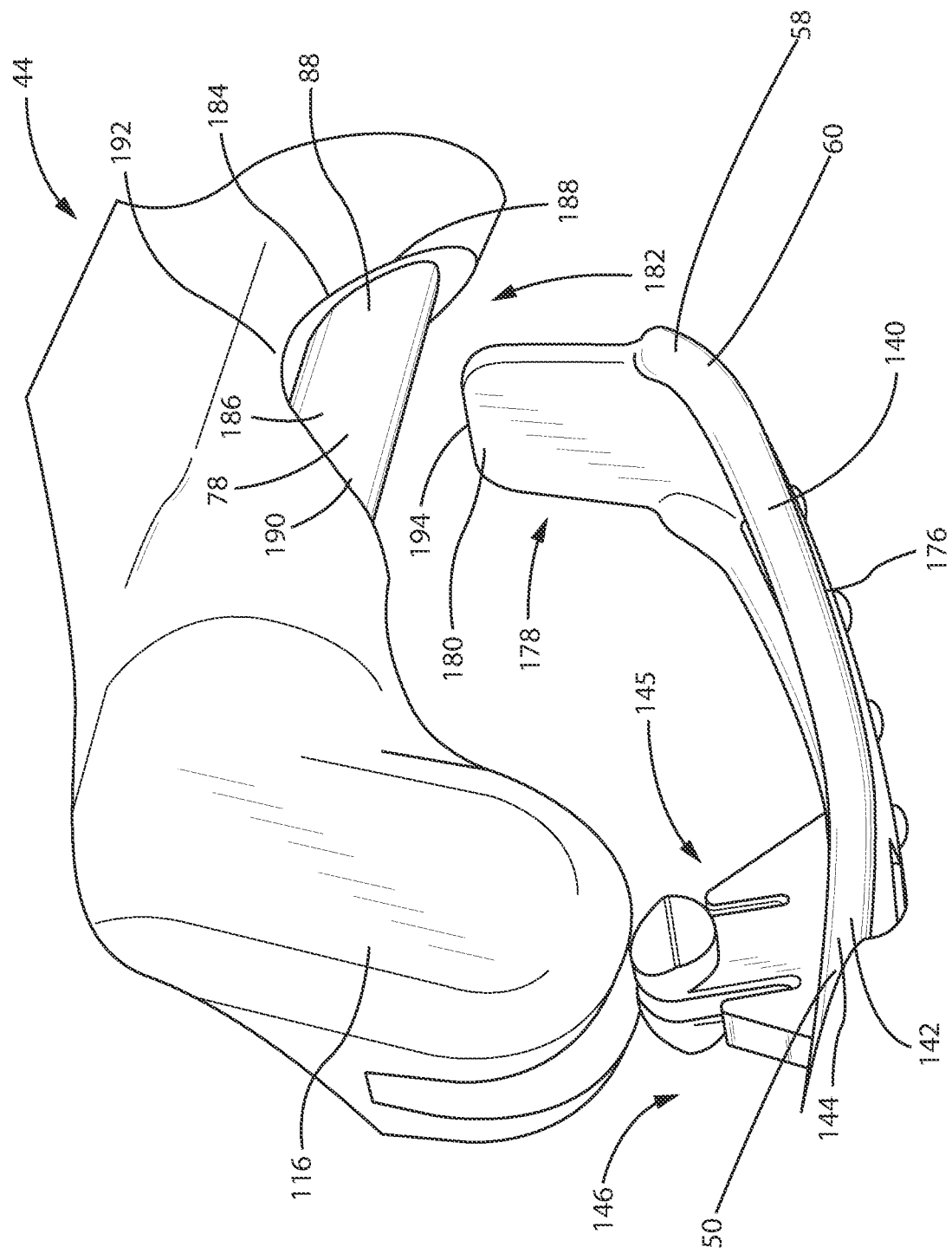
FIG. 11 is an enlarged fragmentary perspective view of a pinch-type irrigation fluid flow obstructing valve formed by compressible irrigation fluid tubing exposed by an opening in the tool frame and a flow obstructing valve actuator of the squeeze hand lever.
Figure 12:
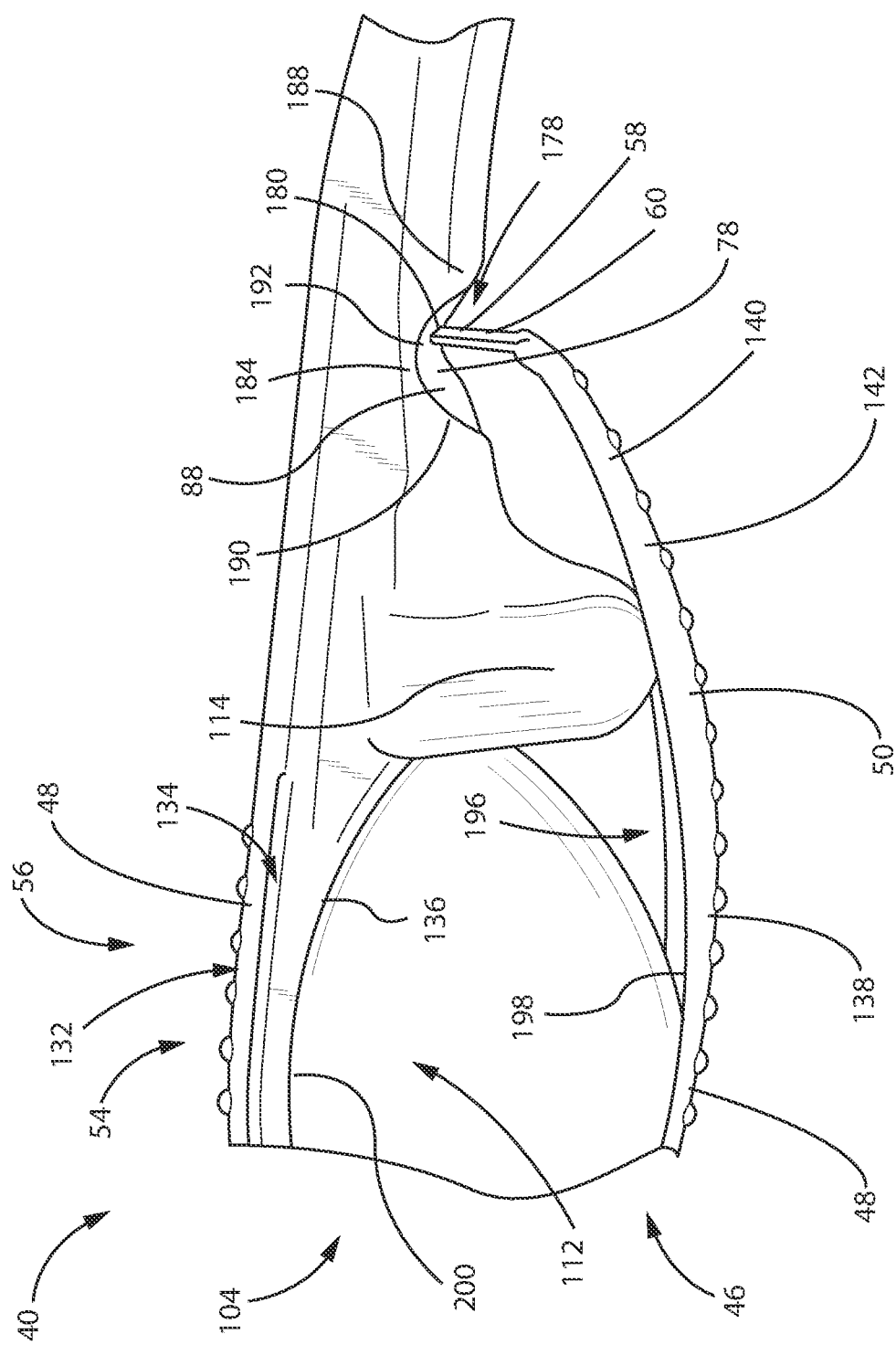
FIG. 12 is a fragmentary side elevation view of the tool depicting the flow obstructing valve actuator of the squeeze hand lever compressing or pinching the exposed irrigation fluid tubing obstructing flow of irrigation fluid discharged from the tool.

With reference to FIG. 10, the squeeze handle lever 142 is an elongate lever arm 144 having an elongate flow obstructing lever arm section 176 extending generally forwardly toward the discharge end of the tool 40 that includes the flow obstructing valve actuator 140 that actuates the flow obstructing valve 58 e.g., pinch valve 60, when forward lever arm section 176 is displaced toward the valve 58 during squeeze handle lever rotation toward the flow obstructing valve actuating position, e.g., flow obstructing position. The flow obstructing valve actuator 140 includes another section of the lever arm 144 that is generally transversely angled, e.g. generally perpendicularly angled, forming a valve actuator effector 178 that preferably actuates the flow obstructing valve 58, e.g., pinch valve 60, by direct contact with the valve 58.

Where the irrigation fluid flow obstructing valve 58 is a pinch-type valve, such as the pinch valve 60 shown in more detail in FIGS. 10-12, the pinch valve 60 preferably is formed by pinching an exposed section of irrigation fluid tubing 88 to block and preferably substantially stop irrigation fluid 52 from being discharged out the tool 40. A preferred pinch valve 60 includes a valve actuating nose 180 disposed at a free end of the valve actuator effector 178 of the squeeze handle lever arm 144 that is received during pinch valve actuation in a recessed pinch valve guide 182 formed by an opening 184 in the frame 44, e.g., opening in frame sidewall, which exposes a compressible segment 186 of the irrigation fluid conduit 78, preferably exposing irrigation fluid tube or tubing 88, which becomes compressed or pinched against part of the frame 44 by the valve actuating nose 180 thereby obstructing irrigation fluid flow. In a preferred embodiment, part of the tubing 88 becomes pinched against part of the irrigation fluid tubing seating channel 128 of one or both frame halves 44a and/or 44b during pinch valve operation.

The valve guide 182 preferably is formed of a plurality of guide walls 188, 190 that converge, such as in the manner depicted in FIG. 11, to a valve seat 192 against which the irrigation fluid tube 88 is compressed by the valve actuating nose 180 to obstruct irrigation fluid flow through the tube 88 when the pinch valve 60 is actuated. In a preferred pinch valve embodiment, the valve guide walls 188, 190 converge to form a generally V-shaped valve guide 182 along which the valve actuating nose 180 can be guided, e.g. slidably guided, toward the valve seat 192 during pinch valve actuation helping to ensure positive seating of the nose 180 generally in line with the seat 192 compressing a portion of the irrigation fluid tube 88 against the seat 192 in the manner depicted in FIG. 12.

During squeezing of the tool handle 56 in a manner that manipulates the handgrip 48 to displace and preferably rotate the squeeze handle lever arm 144 toward the valve actuation position, the nose 180 of the valve actuator effector 178 is received in the pinch valve opening 184 and guided into compressible engagement with the exposed irrigation fluid tube 88 by the valve guide 182 compressing the tube 88 against the valve seat 192. During pinch valve actuation, the exposed tube 88 is compressed against the valve seat 192 by compressing the tube 88 against part of the irrigation fluid tubing seating channel 128 of one or both halves 44a, 44b of the frame 44. As the tube 88 is compressed or pinched, flow of irrigation fluid 52 through the tube 88 toward the discharge port 74 is obstructed and thereby reduced. As pinching pressure is increased by a user squeezing the manipulable handgrip 48 harder, the rate of flow of irrigation fluid 52 out the discharge port 74 can be slowed from a weak stream, to a trickle or even drops of irrigation fluid 52 exiting the port 74 until irrigation fluid flow out the port 74 is substantially completely stopped when the tube 88 is pinched substantially completely closed.

A pinch valve 60 constructed in accordance with the present invention has a pinch valve actuator effector 178 within actuating nose 180 with a generally flat or substantially straight outer irrigation fluid tube compressing edge 194, such as is shown in FIG. 11, but can have a tube compressing edge with a different contour or configuration. In this regard, in one embodiment, the outer irrigation fluid tube compressing edge 194 can have a concave outer edge (not shown) in which a portion of the curved irrigation fluid tube 88 can be received during valve actuation before any compression or pinching of the tube 88 occurs. Such a concave outer edge 194 can help preserve the integrity and life of the tube 88 during repeated pinch valve cycling advantageously extending tool life. Where concave, the outer edge 194 can have a radius of curvature substantially complementary with or even substantially the same as the radius or diameter of the tube 88. In another embodiment, the outer edge 194 can be convex, e.g., be outwardly curved or rounded.

Surge Flow Pump Construction and Operation

As previously disclosed, the surge flow pump 47 is formed by operable cooperation between the flow controlling squeeze handle lever 142 and the portion of the frame 44 capturing the squeeze bulb 104 therebetween compressing the squeeze bulb 104 therebetween during surge flow actuation caused by a user squeezing the handle 56 and manipulating the handgrip 48 displacing, preferably by rotation, the surge flow actuator 138 of the handle lever 142 against the bulb 104 compressing the bulb 104. The handle lever 142 is not only curved along its lengthwise extent, as best shown in FIG. 10, but the handle lever 142 also is curved along a transverse extent, as best shown in FIG. 13 advantageously producing a surge flow pump 47 where the curved handle lever 142 provides pressure displacement of the squeeze bulb 104 when the handle 46 and handgrip 48 are squeezed.

With reference to FIG. 10, the longitudinally concave curved surge flow actuating section 196 of the squeeze handle lever 142 is concave curved facing the squeeze bulb 104 such that compression of the bulb 104 during surge flow actuation increases the surface area of contact between the bulb 104 and handle lever 142 advantageously providing constant pressure displacement of the bulb 104 and pump 47 no matter how big or small the hand of a user grasping the handle 56 and manipulating the handgrip 48. With reference to FIG. 13, the transverse concave curvature of the surge flow actuating section 196 has a concave surface 198 facing the squeeze bulb 104 that generally conforms to the curvature of the curved sidewall 100 of the bulb 104 further maximizing the surface area of contact between the handle lever 142 and bulb 104 during surge flow actuation. This further increases contact surface area further helping to facilitate constant pressure displacement of the bulb 104 during compression or squeezing of the bulb 104 by a user squeezing the handle 56 and urging the curved surge flow actuating section 196 of the handle lever 142 against the bulb 104.

As previously indicated, the squeeze bulb 104 is compressed against a surge flow actuating surface 136 of a substantially rigid reservoir support 134 of the frame 44 that extends alongside the bulb sidewall 100 facilitating surge flow pumping of irrigation fluid from the bulb 104 when the handle lever 142 is squeezed against the bulb 104. A preferred surge flow actuating surface 136 also has a concave curved surface 200 facing the bulb 104 that substantially conforms to the lengthwise curvature of the sidewall 100 of the bulb 104 helping to produce such a constant pressure displacement surge flow pump 47 in accordance with the present invention that is easier and more efficient to use during tool operation. As a result of such a constant pressure displacement surge flow pump construction provided by such a squeeze handle lever 142 having a concave curvature both longitudinally and transversely, compressing the squeeze bulb 104 against a concave curved substantially rigid surge flow actuating surface 136 of the tool frame 44, a surge flow pump 47 is advantageously produced that more completely empties the squeeze bulb 104 during surge flow actuation thereby enabling a greater surge flow rate to be achieved for a longer period of time.

Preferred Combination Suction and Irrigation Tool

With additional reference to FIG. 14, where the tool 40 is equipped with suction and configured as a combination suction and irrigation tool 42 in accordance with the present invention, a tip or free end, e.g., discharge end 64, of the wand 66 the suction inlet port 76 preferably is axially outwardly offset relative to the irrigation fluid discharge port 74 forming a suction tip 202 that makes contact with the area sought to be suctioned, e.g., tissue, etc., before the recessed irrigation fluid discharge port 74 does. With continued reference to FIG. 14, the suction inlet port 76 has an inlet port opening 204 formed in the axial end 206 of the suction tip 202 facing in a longitudinal or axial direction relative to the wand 66. The suction tip 202 preferably is a generally cylindrical section of the wand 66 that extends outwardly beyond an axial end 203 of the wand 66 in which the irrigation fluid discharge port 74 is disposed that forms an irrigation fluid discharging tip 205.

The suction tip 202 can and preferably does include a plurality of spaced apart generally transversely extending suction inlets 208, 210 smaller in within diameter than the primary inlet port opening 204 to enable an area or volume greater than the area surrounding the primary inlet port opening 204 to be suctioned. In a preferred embodiment, the suction tip 202 has a plurality of axially spaced suction inlets 208, 210 formed in one side of the tip 202 and a plurality of axially spaced suction inlets 208, 210 formed in an opposite side of the tip 202 with only one side of the tip 202 and corresponding suction inlets 208, 210 formed therein shown in FIG. 14.

The suction tip 202, including the primary inlet port opening 204 of the suction inlet port 76 also is transversely or outwardly offset from the irrigation fluid discharge port 74 such that the suction inlet port 76 is thereby vertically offset above the irrigation fluid discharge port 74 during tool operation where the tool is oriented with the squeeze bulb 104 towards the floor during tool use. This over-under orientation with the suction tip 202 on top of the irrigation fluid tip 205 not only facilitates the suction tip 202 making first contact with the area, e.g., tissue, etc., sought to be suctioned but also enables irrigation fluid 52 to be discharged from the irrigation fluid discharge port 74 without the fluid 52 immediately being sucked back into the suction inlet port 76. In addition, the wand 66 preferably is configured such that the irrigation fluid discharge port 74 includes a flow directing nozzle 214 formed in the axial end 203 of the irrigation fluid discharge tip 205 that discharges a stream of irrigation fluid 52 along a flow axis 216 disposed at an acute included angle relative to a central axis 218 of the suction inlet port 74 further preventing freshly discharged irrigation fluid 52 from being sucked back into the suction inlet port 74 during tool operation.

Understandably, the present invention has been described above in terms of one or more preferred embodiments and methods. It is recognized that various alternatives and modifications may be made to these embodiments and methods that are within the scope of the present invention. Various alternatives are contemplated as being within the scope of the present invention. It is also to be understood that, although the foregoing description and drawings describe and illustrate in detail one or more preferred embodiments of the present invention, to those skilled in the art to which the present invention relates, the present disclosure will suggest many modifications and constructions, as well as widely differing embodiments and applications without thereby departing from the spirit and scope of the invention.

What is claimed is:

1. An irrigation fluid dispensing tool comprising:
    (a) a frame comprising (1) an irrigation fluid conduit having an irrigation fluid discharge port at one end of the irrigation fluid conduit, and (2) a suction fluid conduit having one end in fluid-flow communication with a suction inlet port;
    (b) a manipulable handgrip comprised of an irrigation fluid flow controller in operable cooperation with the frame;
    (c) an irrigation fluid surge pump actuated by the irrigation fluid flow controller when the irrigation fluid flow controller is disposed in a surge fluid pump actuating position; and
    (d) an irrigation fluid flow obstructing valve actuated by the irrigation fluid flow controller when the irrigation fluid flow controller is disposed in an irrigation fluid flow obstructing position, the irrigation fluid flow obstructing valve disposed between the irrigation fluid surge pump and the irrigation fluid discharge port, the irrigation fluid flow obstructing valve configured to obstruct irrigation fluid flow out the irrigation fluid discharge port when the irrigation fluid flow controller is disposed in the irrigation fluid flow obstructing position.

2. The tool of claim 1, wherein the irrigation fluid flow controller further comprises an irrigation fluid flow initiating position where the irrigation fluid flow controller is disposed in an intermediate position between the surge fluid pump actuating position and the irrigation fluid flow obstructing position.

3. The tool of claim 2, wherein a baseline rate of flow of irrigation fluid from the tool occurs when the irrigation fluid flow controller is in the irrigation fluid flow initiating position.

4. The tool of claim 3, wherein a surge rate of flow of irrigation fluid from the tool is produced when the irrigation fluid flow controller is in the surge fluid pump actuating position and the manipulable handgrip is squeezed.

5. The tool of claim 4, wherein the surge rate of flow is at least a plurality of times the baseline rate of flow.

6. The tool of claim 5, wherein the surge rate of flow is greater than the baseline rate of flow and proportional to the amount of squeezing pressure applied to the manipulable handgrip.

7. The tool of claim 2, wherein the irrigation fluid surge pump comprises (1) a compressible irrigation fluid reservoir, and (2) a one-way irrigation fluid flow valve in fluid-flow communication with the compressible irrigation fluid reservoir and the irrigation fluid flow obstructing valve, the one-way irrigation fluid flow valve configured to prevent irrigation fluid exiting from the compressible irrigation fluid reservoir from flowing back into the compressible irrigation fluid reservoir.

8. The tool of claim 5, wherein the surge rate of flow is at least three times the amount of baseline rate of flow.

9. The tool of claim 7, wherein the one-way irrigation fluid flow valve comprises a check valve disposed upstream of the irrigation fluid flow obstructing valve and downstream of the compressible irrigation fluid reservoir.

10. The tool of claim 1, wherein the irrigation fluid surge pump comprises (1) a compressible irrigation fluid reservoir, (2) a first one-way irrigation fluid flow valve in fluid-flow communication with the irrigation fluid flow obstructing valve and compressible irrigation fluid reservoir, the first one-way irrigation fluid flow valve disposed upstream of the irrigation fluid flow obstructing valve, and (3) a second one-way irrigation fluid flow valve in fluid-flow communication with the compressible irrigation fluid reservoir, the second one-way irrigation fluid flow valve disposed upstream of the compressible irrigation fluid reservoir.

11. The tool of claim 5, wherein the surge rate of flow occurs for at least three seconds.

12. The tool of claim 2, wherein the irrigation fluid flow obstructing valve comprises a pinch valve that is compressed by the irrigation fluid flow controller when the irrigation fluid flow controller is disposed in the irrigation fluid flow obstructing position, the pinch valve obstructing irrigation fluid flow through the irrigation fluid conduit to the irrigation fluid discharge port when compressed by the irrigation fluid flow controller disposed in the irrigation fluid flow obstructing position.

13. The tool of claim 12, wherein the pinch valve further comprises:
    an elongate longitudinally extending irrigation fluid tubing seating channel;
    an elastomeric irrigation fluid tube seated within the elongate longitudinally extending irrigation fluid tubing seating channel; and
    the irrigation fluid flow controller comprises a flow obstructing lever arm section;
    wherein the flow obstructing lever arm section compresses the elastomeric irrigation fluid tube in the irrigation fluid flow obstructing position when the irrigation fluid flow controller is disposed in the irrigation fluid flow obstructing position.

14. The tool of claim 13, wherein the pinch valve further comprises:
    the valve actuating nose disposed at a free end of the flow obstructing lever arm section;

a recessed pinch valve guide formed by an opening in the elongate longitudinally extending irrigation fluid tubing seating channel;

a compressible segment of the elastomeric irrigation fluid tube;

wherein the valve actuating nose compresses the compressible segment against the elongate longitudinally extending irrigation fluid tubing seating channel in the irrigation fluid flow obstructing position.

15. The tool of claim 2, wherein the manipulable handgrip comprises a handle in operable cooperation with the frame, the handle configured to pivot about a portion of the handle between the (i) surge fluid pump actuating position, (ii) irrigation fluid initiating position, and (iii) irrigation flow obstructing position.

16. The tool of claim 15, wherein the frame is configured for one-handed manipulation between the irrigation fluid flow obstructing position, the irrigation fluid flow initiating position, and the surge pump actuating position; wherein the irrigation fluid surge pump comprises a compressible irrigation fluid reservoir carried by the frame; and wherein the handle comprises a pivotable lever operably coupled by a pivot to the frame, the pivotable lever having (a) a first portion disposed on one side of the pivot and comprising a surge fluid pump actuator configured to compress the compressible irrigation fluid reservoir to discharge surge flow of irrigation fluid therefrom when the first portion of the lever is manually urged toward the compressible irrigation fluid reservoir compressing the compressible irrigation fluid reservoir, and (b) a second portion disposed on an opposite side of the pivot and comprising a flow obstructing valve actuator configured to actuate the irrigation fluid flow obstructing valve when the second portion of the lever is manually urged toward the irrigation fluid flow obstructing valve.

17. The tool of claim 1, wherein the manipulable handgrip comprises a handle in operable cooperation with the frame, the handle configured to pivot about a portion of the handle between the (i) surge fluid pump actuating position, and (ii) irrigation flow obstructing position.

18. An irrigation fluid dispensing tool comprising:
(a) a frame comprising an irrigation fluid conduit and an irrigation fluid discharge port at a free end of the irrigation fluid conduit out which irrigation fluid is dispensed from the irrigation fluid dispensing tool;
(b) a compressible irrigation fluid reservoir carried by the frame, the compressible irrigation fluid reservoir having an inlet and an outlet,
(c) a handle that includes a manipulable handgrip comprised of an irrigation fluid flow controller, the handle disposed in operable cooperation with the frame and the compressible irrigation fluid reservoir,
(d) a first one-way irrigation fluid flow valve in fluid-flow communication with the inlet of the compressible irrigation fluid reservoir and disposed upstream of the compressible irrigation fluid reservoir;
(e) a second one-way irrigation fluid flow valve in fluid-flow communication with the outlet of the compressible irrigation fluid reservoir and disposed downstream of the compressible irrigation fluid reservoir;
(f) an irrigation fluid flow obstructing valve in fluid flow communication with the outlet of the compressible irrigation fluid reservoir, the irrigation fluid flow obstructing valve disposed downstream of the outlet of the compressible irrigation fluid reservoir and downstream of the second one-way irrigation fluid flow valve;
wherein the handle is pivotable between:

(1) a flow obstructing actuation position actuating the irrigation fluid flow obstructing valve and obstructing irrigation fluid from flowing out the irrigation fluid discharge port; and
(2) a flow initiating position initiating flow of irrigation fluid from the compressible irrigation fluid reservoir through the irrigation fluid conduit and out the irrigation fluid discharge port; and
(3) a surge flow actuating position discharging a surge flow of irrigation fluid through the irrigation fluid conduit and out the irrigation fluid discharge port.

19. The tool of claim 18, wherein the handle is pivotably coupled to the frame and pivotable relative to the frame between:
(1) the flow obstructing actuation position;
(2) the flow initiating position; and
(3) the surge flow actuation position;
wherein the flow initiating position has an initial rate of flow of irrigation fluid;
wherein the surge flow actuation position has a surge rate of flow of irrigation fluid; and
wherein the surge rate of flow is greater than the initial rate of flow.

20. The tool of claim 19, further comprising a pinch valve actuated by the handle when the handle is disposed in an irrigation fluid flow obstructing position.

21. The tool of claim 20, wherein the pinch valve further comprises:
the handle comprised of a valve actuator effector having a valve actuating nose with an irrigation fluid tube compressing edge;
an irrigation fluid conduit having a compressible segment, where the irrigation fluid conduit is mounted within a fluid tubing seating channel; and
an elongate longitudinally extending irrigation fluid tubing seating channel having an opening formed therein that defines a valve seat; and
wherein the irrigation fluid tube compressing edge of the handle is received in the opening and seats in the valve seat compressing the compressible segment of the irrigation fluid conduit against the elongate longitudinally extending irrigation fluid tubing seating channel opposing irrigation fluid flow therethrough when the handle is disposed in the flow obstructing actuation position.

22. The tool of claim 18, further comprising:
at least one guide wall located adjacent the opening; and
a pivot fulcrum where the handle mounts to the frame; and
wherein the handle pivots about the pivot fulcrum from:
the flow obstructing actuation position; and to
the flow initiating position.

23. The tool of claim 18, further comprising an elongate suction fluid conduit formed in the frame, the suction fluid conduit having one end in fluid-flow communication with a suction inlet port, the suction inlet port extending outwardly of the irrigation fluid discharge port and overlying the irrigation fluid discharge port.

24. The tool of claim 23, wherein the suction inlet port extends outwardly of the irrigation fluid discharge port and overlies the irrigation fluid discharge port.

25. The tool of claim 24, further comprising (a) a first pair of axially spaced apart suction inlets adjacent the suction inlet port, the first pair of suction inlets extending outwardly from and oriented generally transversely relative to the suction conduit, the first pair of suction inlets disposed on one side of the suction inlet port, and (b) a second pair of axially spaced apart suction inlets adjacent the suction inlet port, the first pair of suction inlets extending outwardly from and oriented generally transversely relative to the suction conduit, the first pair of suction inlets disposed on the opposite side of the suction inlet port.

26. The tool of claim 22, wherein the frame comprises a fulcrum-receiving socket formed therein configured for receiving the pivot fulcrum therein, the socket configured to provide a shipping retainer position that spaces the lever from the compressible irrigation fluid reservoir while preventing pivoting of the lever, and an operating position that permits rotation of the lever, wherein the pivot fulcrum extends outwardly from the lever and is configured to be received in the fulcrum-receiving pocket, releasably retained in the shipping retainer position where the lever is disposed alongside but spaced from the compressible irrigation fluid reservoir, and displaced from the shipping or storage retainer position to the operating position moving the lever closer to the compressible irrigation fluid reservoir where the lever is pivotable about the fulcrum between (1) the flow obstructing actuation position; (2) the flow initiating position; and (3) the surge flow actuation position.

27. The tool of claim 18, wherein operable cooperation of the handle with the compressible irrigation fluid reservoir defines a constant pressure displacement irrigation fluid pump.

28. The tool of claim 27, wherein the compressible irrigation fluid reservoir comprises a squeeze bulb having a convex longitudinally curved sidewall, wherein the handle has a concave longitudinally curved surface facing the squeeze bulb generally conforming to the convex longitudinally curved sidewall of the squeeze bulb, and wherein a portion of the handle bears against the convex longitudinally curved sidewall of the squeeze bulb to compress and displace irrigation fluid therefrom when the lever is disposed in either the flow initiating position or the surge flow actuation position.

29. The tool of claim 18, wherein operable cooperation of the handle with the compressible irrigation fluid reservoir defines an irrigation fluid pump configured to vary irrigation fluid flow discharged from the tool ranging from a surge of irrigation fluid, a steady stream of irrigation fluid, a trickle of irrigation fluid, and drops of irrigation fluid.

30. The tool of claim 18, wherein the tool is operated without any electrical power.

31. The tool of claim 1, wherein the irrigation fluid surge pump comprises a constant pressure displacement irrigation fluid surge pump.

32. The tool of claim 31, wherein the compressible irrigation fluid reservoir comprises a squeeze bulb.

33. The tool of claim 6, wherein the irrigation fluid surge pump comprises a constant pressure displacement irrigation fluid surge pump.

34. The tool of claim 33, wherein the tool is operated without any electrical power.

35. The tool of claim 1, wherein the frame comprises an elongate curved wand having the irrigation fluid conduit and the suction fluid conduit formed therein, the suction fluid conduit having a length greater than the irrigation fluid conduit thereby positioning the suction inlet port outwardly beyond the irrigation fluid discharge port, and the suction inlet port disposed above the irrigation fluid discharge port.

36. The tool of claim 1, wherein the irrigation fluid conduit has an irrigation fluid discharging tip with the irrigation fluid discharge port formed in an axial end thereof, the suction fluid conduit has a suction tip with the suction inlet port formed in an axial end thereof, the suction tip extending outwardly beyond the irrigation fluid discharging tip, the suction tip having a plurality of plurality of spaced apart suction inlets formed therein, each suction inlet in fluid-flow communication with the suction fluid conduit and disposed at an angle relative to the suction inlet port.

37. The tool of claim 36, wherein each suction inlet port is oriented generally transversely relative to the suction fluid conduit and relative to the suction intake port.

38. The tool of claim 1, wherein the irrigation fluid conduit has an irrigation fluid discharging tip with the irrigation fluid discharge port formed in an axial end thereof and defining an irrigation fluid flow directing nozzle, the suction fluid conduit has a suction tip with the suction inlet port formed in an axial end thereof, the suction tip extending outwardly of and beyond the irrigation fluid discharging tip positioning the suction inlet port outwardly of and beyond the irrigation fluid flow directing nozzle, the irrigation fluid flow directing nozzle configured to discharge a stream of irrigation fluid therefrom along a flow axis disposed at an acute angle relative to a central axis of the suction inlet port configured to prevent irrigation fluid from being sucked into the suction inlet port upon the irrigation fluid being discharged from the irrigation fluid flow directing nozzle.

39. The tool of claim 1, wherein the frame comprises an elongate curved wand having the irrigation fluid conduit formed therein and extending to an irrigation fluid discharging tip in which the irrigation fluid discharge port is formed in a free end thereof, the suction fluid conduit formed therein and extending to a suction tip in which the suction inlet port is formed in a free end thereof, the suction tip extending outwardly of and beyond the irrigation fluid discharging tip, the suction tip having a plurality of spaced apart suction inlets formed therein, each suction inlet extending generally radially outwardly from the suction fluid conduit, and each suction inlet disposed adjacent the suction inlet port.

40. The tool of claim 7, wherein the irrigation fluid surge pump is configured to vary irrigation fluid flow discharged from the tool ranging from a surge of irrigation fluid, a steady stream of irrigation fluid, a trickle of irrigation fluid, and drops of irrigation fluid.

* * * * *